US011529167B2

(12) United States Patent
Kiev

(10) Patent No.: US 11,529,167 B2
(45) Date of Patent: Dec. 20, 2022

(54) DEVICE AND METHOD FOR ACCESS TO INTERIOR BODY REGIONS

(71) Applicant: AOK Innovations, LLC, Lexington, KY (US)

(72) Inventor: Jon Kiev, Lexington, KY (US)

(73) Assignee: AOK Innovations, LLC, Lexington, KY (US)

( * ) Notice: Subject to any disclaimer, the term of this patent is extended or adjusted under 35 U.S.C. 154(b) by 583 days.

(21) Appl. No.: 16/782,689

(22) Filed: Feb. 5, 2020

(65) Prior Publication Data

US 2020/0170667 A1 Jun. 4, 2020

Related U.S. Application Data

(60) Division of application No. 15/653,498, filed on Jul. 18, 2017, now Pat. No. 10,588,658, which is a continuation-in-part of application No. 14/809,214, filed on Jul. 25, 2015, now Pat. No. 9,743,952.

(51) Int. Cl.
*A61B 17/34* (2006.01)
*A61B 17/3209* (2006.01)
*A61B 17/00* (2006.01)

(52) U.S. Cl.
CPC .... *A61B 17/3417* (2013.01); *A61B 17/32093* (2013.01); *A61B 17/34* (2013.01); *A61B 17/3415* (2013.01); *A61B 17/3462* (2013.01); *A61B 17/3474* (2013.01); *A61B 17/3494* (2013.01); *A61B 17/3496* (2013.01); *A61B 2017/00809* (2013.01); *A61B 2017/346* (2013.01); *A61B 2017/3456* (2013.01)

(58) Field of Classification Search
CPC ............ A61B 17/3476; A61B 17/3415; A61B 17/3496; A61B 17/3494; A61B 17/32093; A61B 17/3417; A61B 2017/346; A61M 25/0612; A61M 29/00
See application file for complete search history.

(56) References Cited

U.S. PATENT DOCUMENTS

| 4,535,773 | A | 8/1985 | Yoon |
| 5,066,288 | A | 11/1991 | Deniega et al. |
| 5,152,754 | A | 10/1992 | Plyley et al. |
| 5,295,977 | A | 3/1994 | Cohen et al. |

(Continued)

FOREIGN PATENT DOCUMENTS

| CN | 2252603 | 4/1997 |
| EP | 0135364 A2 | 3/1985 |
| WO | WO 2014/006403 A1 | 1/2014 |

*Primary Examiner* — Diane D Yabut
*Assistant Examiner* — Christina C Lauer
(74) *Attorney, Agent, or Firm* — Marshall, Gerstein & Borun LLP

(57) ABSTRACT

A device and method is provided to gain access to interior body regions. The system includes a safety needle assembly, a stylet assembly, a blade assembly, an obturator assembly, and a dilator assembly. The safety needle assembly or stylet assembly accesses an interior body region, after which the blade assembly expands the pathway created by the safety needle assembly or stylet assembly. The obturator then further expands the pathway and delivers the dilator assembly to the desired location. The safety needle assembly, obturator assembly, and blade assembly are removed, leaving the dilator assembly in place for future procedures.

7 Claims, 19 Drawing Sheets

(56) References Cited

U.S. PATENT DOCUMENTS

| | | | |
|---|---|---|---|
| 5,314,417 A | 5/1994 | Stephens et al. | |
| 5,342,382 A | 8/1994 | Brinkerhoff et al. | |
| 5,387,197 A | 2/1995 | Smith et al. | |
| 5,522,833 A | 6/1996 | Stephens et al. | |
| 5,624,459 A | 4/1997 | Kortenbach et al. | |
| 5,674,237 A | 10/1997 | Ott | |
| 5,779,680 A | 7/1998 | Yoon | |
| 5,843,115 A | 12/1998 | Morejon | |
| 5,855,566 A | 1/1999 | Dunlap et al. | |
| 5,879,332 A * | 3/1999 | Schwemberger | A61B 17/3496 604/164.08 |
| 5,984,941 A | 11/1999 | Wilson et al. | |
| 6,017,356 A * | 1/2000 | Frederick | A61B 17/3417 606/167 |
| 6,056,766 A | 5/2000 | Thompson | |
| 6,063,099 A | 5/2000 | Danks et al. | |
| 6,156,006 A | 12/2000 | Brosens et al. | |
| 6,402,770 B1 | 6/2002 | Jessen | |
| 6,447,527 B1 | 9/2002 | Thompson et al. | |
| 6,613,063 B1 | 9/2003 | Hunsberger | |
| 7,344,519 B2 | 3/2008 | Wing et al. | |
| 7,367,960 B2 | 5/2008 | Stellon et al. | |
| 7,419,496 B2 | 9/2008 | Staudner | |
| 7,731,730 B2 | 6/2010 | Popov | |
| 8,419,764 B2 | 4/2013 | Begg | |
| 8,801,741 B2 | 8/2014 | Ahlberg et al. | |
| 8,940,007 B2 | 1/2015 | Smith et al. | |
| 9,743,952 B2 | 8/2017 | Kiev | |
| 9,743,953 B2 | 8/2017 | Kiev | |
| 2007/0270819 A1 | 11/2007 | Justis et al. | |
| 2008/0009894 A1 | 1/2008 | Smith | |
| 2012/0116418 A1* | 5/2012 | Belson | A61B 17/3403 606/139 |
| 2016/0235435 A1 | 8/2016 | Kiev | |

\* cited by examiner

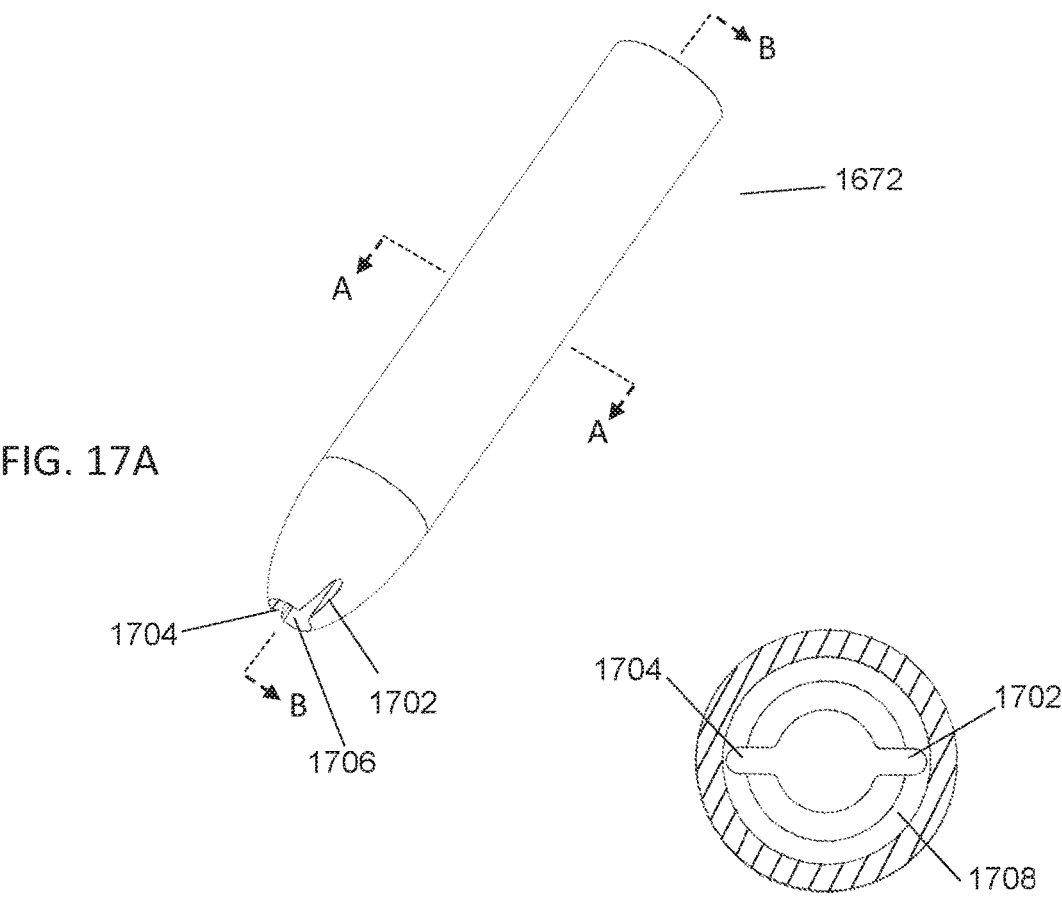
FIG. 17A
FIG. 17B
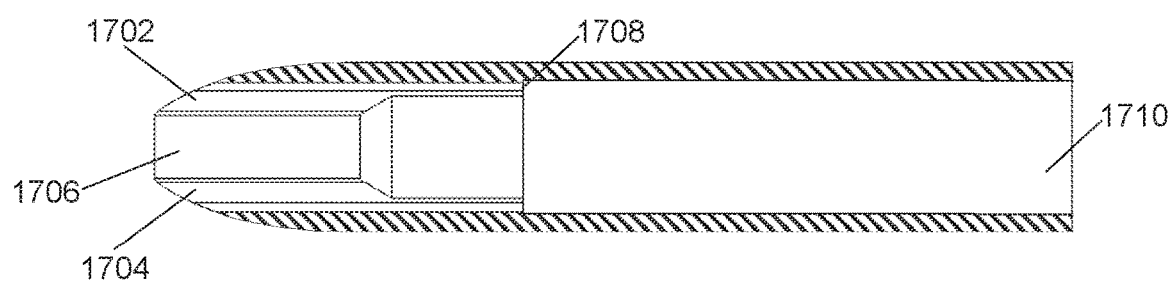
FIG. 17C

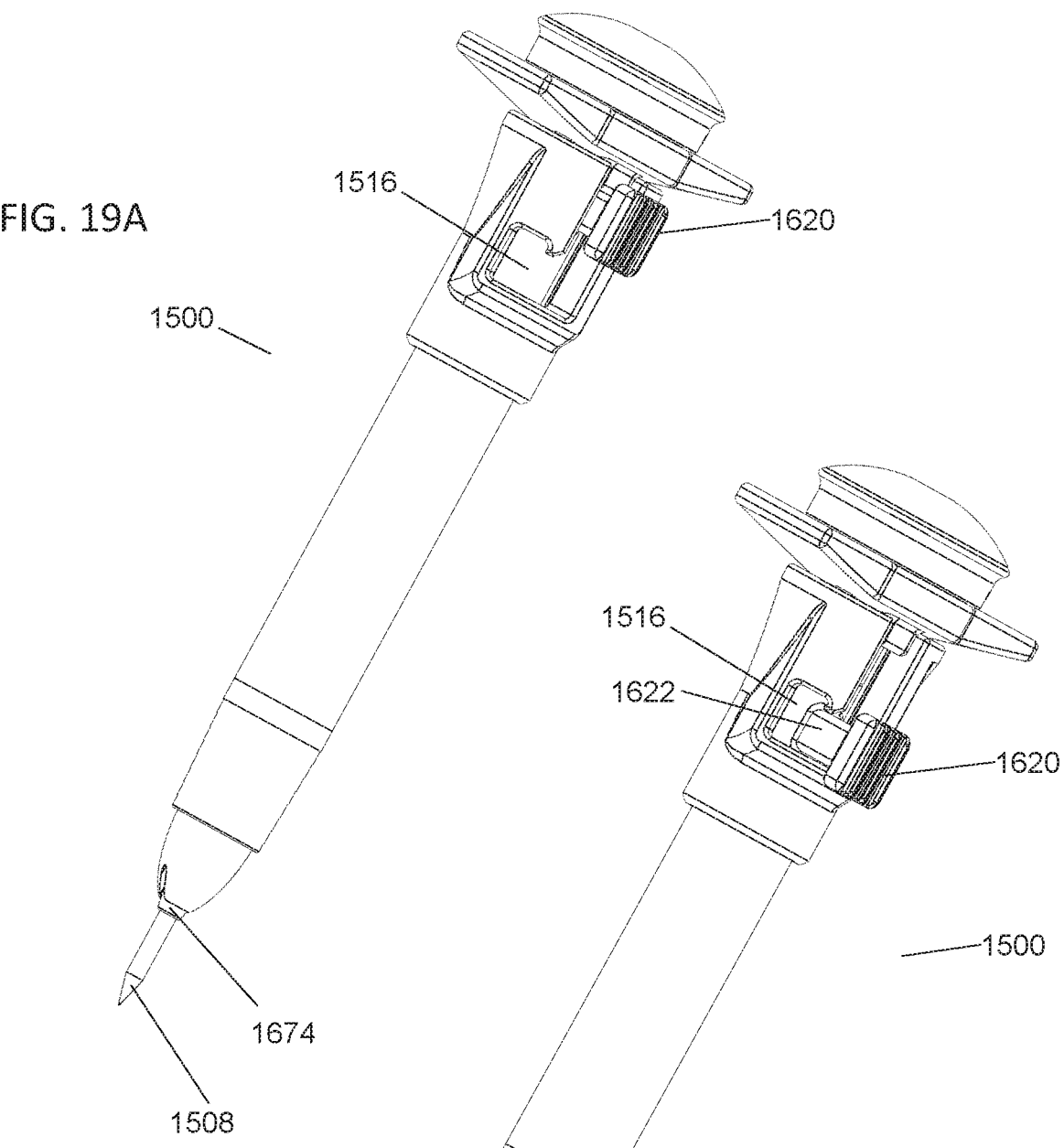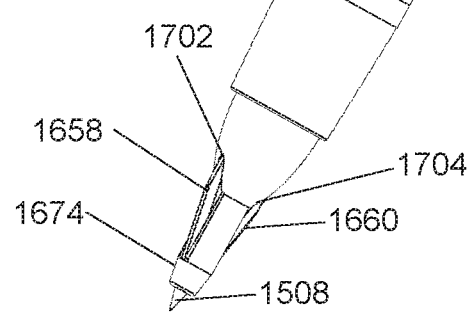

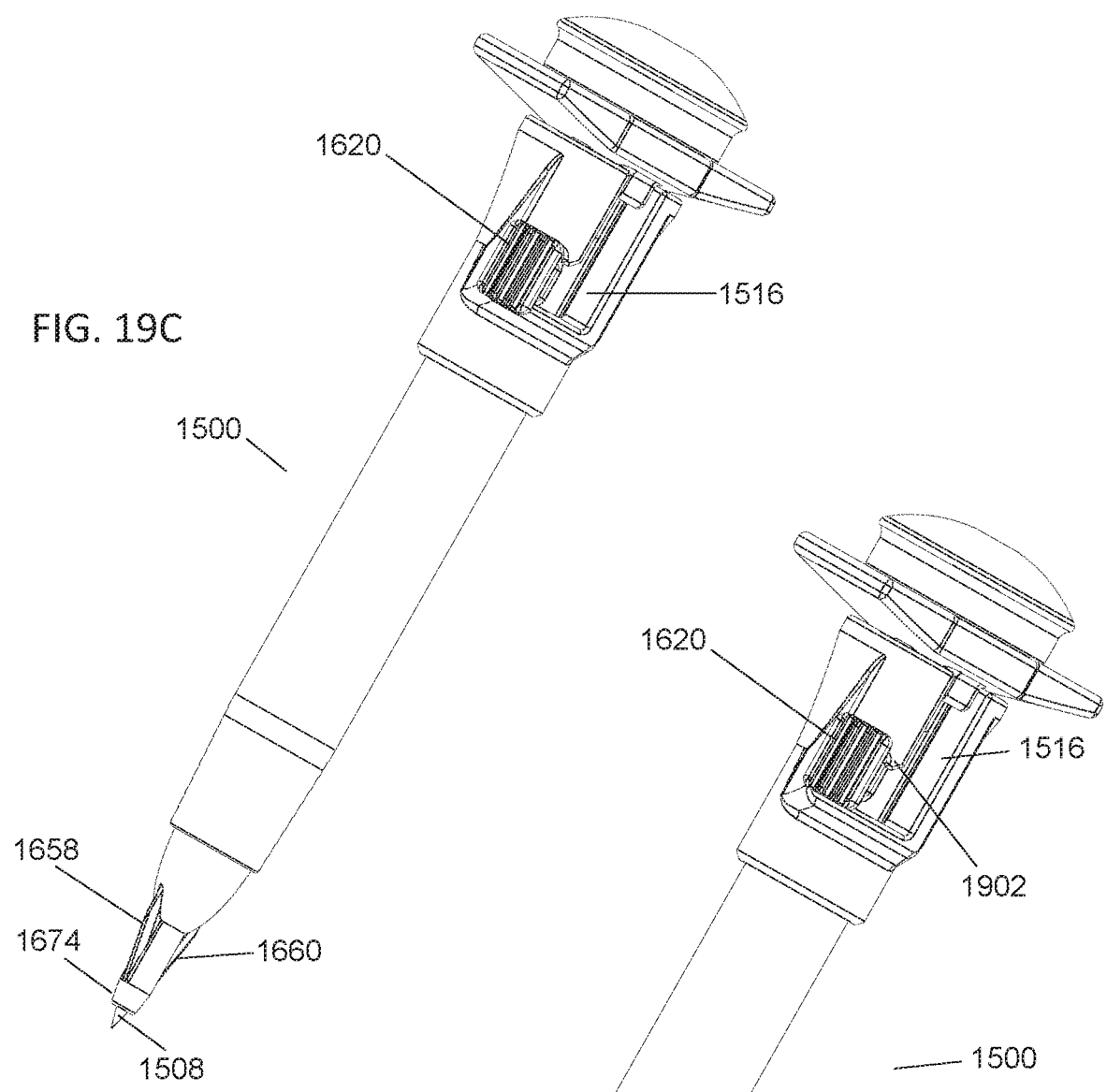

DEVICE AND METHOD FOR ACCESS TO INTERIOR BODY REGIONS

CROSS-REFERENCE TO RELATED APPLICATIONS

This application is a divisional of U.S. patent application Ser. No. 15/653,498, filed Jul. 18, 2017, which is a continuation-in-part of, and claims priority to, U.S. patent application Ser. No. 14/809,214, filed Jul. 25, 2015, which issued as U.S. Pat. No. 9,743,952. Each of U.S. patent application Ser. Nos. 15/653,498 and 14/809,214 is incorporated by reference herein in its entirety.

TECHNICAL FIELD

The present invention relates to devices and methods to access interior body regions. More particularly, it relates to devices and methods used to create space to insert a tube into a patient.

BACKGROUND

Embodiments of the invention relate to devices to create access to interior body regions and methods of using the devices.

There are many instances in which a practitioner must access the chest, abdomen, or pelvis, and insert a drainage tube, or chest tube. Examples of these instances include: collapsed lung, lung infection, bleeding in the chest cavity, fluid or air buildup due to other medical conditions or trauma, and prior surgery.

The traditional way of inserting a chest tube begins with the practitioner prepping the side of the body for the chest tube by sterilizing the area. Using a scalpel, the practitioner then makes a small incision (skin nick), between the ribs closest to the desired location in the chest. Then, using a combination of blunt dissection and surgical clamps, the practitioner will slowly open the space and extend it into the chest cavity. Once the practitioner confirms she has reached the desired space, the chest tube is inserted and sutured in place to prevent slippage.

Critics claim that the traditional method of chest tube insertion is barbaric and does not take advantage of advances in technology that can make the insertion process safer and more effective. Some companies have designed devices, called trocars, to facilitate safer and easier chest tube placement without using multiple, separate components.

Many groups of trocars include a combination of an access needle, an obturator and a dilator. The doctor advances the device against the skin and interior body regions using the access needle. As the doctor advances the device through the body, the obturator expands the pathway created by the access needle. When the device reaches the desired area, the practitioner removes the safety needle and the obturator from the dilator, leaving the dilator in place. The practitioner then pushes the chest tube through the dilator and removes the dilator, leaving the chest tube in the desired location.

Problems arise with these types of trocars, however, because the obturator does not actually work very well in expanding the pathway created by the relatively small access needle. The skin provides a tough membrane that resists expansion, and additional skin nicks (using a separate scalpel) are required around the access needle to allow the obturator to properly expand the skin layer and continue to penetrate deeper into the body.

To address this issue, other groups of trocars employ a retractable blade instead of an access needle. The blade is used to create a larger skin nick and advance through other tissues as needed until reaching the desired location. The obturator easily expands the pathway as it passes through the skin layer while the practitioner advances the device, and then the blade is retracted and the blade/obturator combination is removed, leaving the dilator in place for the chest tube.

While these groups of trocars address the issue of requiring an additional scalpel to allow the obturator to expand the skin layer, they do not include the access needle that prevents the doctor from progressing too quickly or too far and causing harm to the patient. Without the access needle as part of the system, the patient is at a greater risk of complications.

What is needed in the market is an all-in-one trocar device that provides the ability to create a skin nick and maintain safety as the device is inserted deeper into the body, while quickly accessing the desired location for chest tube placement.

BRIEF SUMMARY OF THE INVENTION

Benefits achieved in accordance with principles of the disclosed invention include a device that provides access to interior body regions.

Some aspects of the present invention relate to a safety needle assembly, a blade assembly, an obturator assembly, and a dilator assembly. The safety needle assembly, blade assembly, obturator assembly, and dilator assembly are assembled to create an access device.

In some aspects of the present invention, the blade assembly includes multiple blades, while in other aspects of the present invention, the blade assembly includes a single blade.

In other aspects of the present invention, the safety needle assembly includes a hub through which fluid may be drawn in order to confirm the device has reached the proper location within the body.

In further aspects of the present invention, the blade assembly and safety needle assembly are longitudinally coaxial, while in still further aspects of the present invention, the blade assembly and safety needle assembly are not longitudinally coaxial.

Yet other aspects of the present invention relate to a method of accessing interior body regions in which the safety needle assembly is advanced through skin and into interior body regions to create a pathway. The blades of the blade assembly are deployed and the blade assembly is advanced into the skin to create a skin nick, after which the blades are retracted. The access device is then advanced into the tissue, and the obturator assembly increases the diameter of the pathway created by the safety needle. After the access device is in the proper location, the safety needle assembly, blade assembly, and obturator assembly are removed from the dilator assembly, leaving the dilator assembly in the body to provide a conduit through which other devices may be inserted.

Some other aspects of the present invention relate to a stylet assembly, a blade assembly, a pushrod, an obturator assembly, and a dilator assembly. The stylet assembly, blade assembly, pushrod, obturator assembly, and dilator assembly are assembled to create an access device.

In other aspects of the present invention, the user manipulates the pushrod to deploy and retract the blade assembly Yet other aspects of the present invention relate to a method of accessing interior body regions in which the stylet assembly is advanced through skin and into interior body regions to create a pathway. The blades of the blade assembly are deployed by manipulating the pushrod and the blade assembly is advanced into the skin to create a skin nick, after which the blades are retracted by manipulating the pushrod. The access device is then advanced into the tissue, and the obturator assembly increases the diameter of the pathway created by the stylet assembly. After the access device is in the proper location, the stylet assembly, blade assembly, and obturator assembly are removed from the dilator assembly, leaving the dilator assembly in the body to provide a conduit through which other devices may be inserted.

BRIEF SUMMARY OF THE DRAWINGS

The accompanying drawings, which are incorporated in and form a part of the specification, illustrate example embodiments and, together with the description, serve to explain the principles of the invention. In the drawings:

FIGS. 17A-C illustrate isometric and cross-sectional views of an obturator bottom of another alternate embodiment of an insertion device according to aspects of the present invention;

FIGS. 19A-D illustrate various steps used to insert another alternate embodiment of an insertion device according to aspects of the present invention.

DETAILED DESCRIPTION

Figure 1:
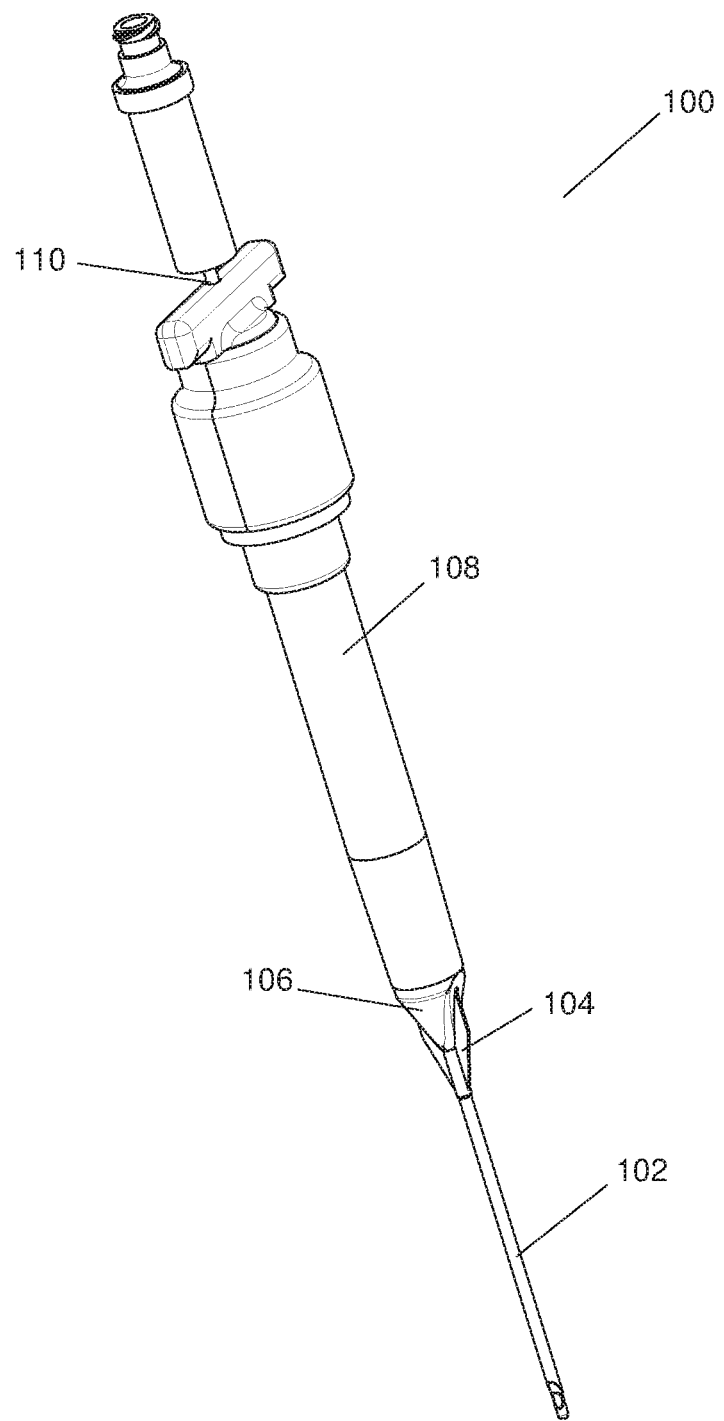
FIG. 1 illustrates an insertion device according to aspects of the present invention.

FIG. 1 illustrates an insertion device according to aspects of the present invention.

As shown in the figure, insertion device 100 includes safety needle 102, blade assembly 104, obturator assembly 106, dilator assembly 108, and handle hole 110.

Specific aspects of safety needle 102, blade assembly 104, obturator assembly 106, and dilator assembly 108 will be further described with reference to FIGS. 2, 3, 4, and 8, respectively.

In general, insertion device 100 is assembled by inserting safety needle assembly 102 through handle hole 110 and into blade assembly 104 until safety needle assembly 102 is distal to the distal end of blade assembly 104. Then, the combination of safety needle assembly 102 and blade assembly 104 is inserted through obturator assembly 106. Then, obturator assembly 106, blade assembly 104, and safety needle assembly 102 are connected to dilator assembly 108. A more detailed description of the assembly and operation of insertion device 100 will be further described with reference to FIGS. 2-8.

Figure 2:
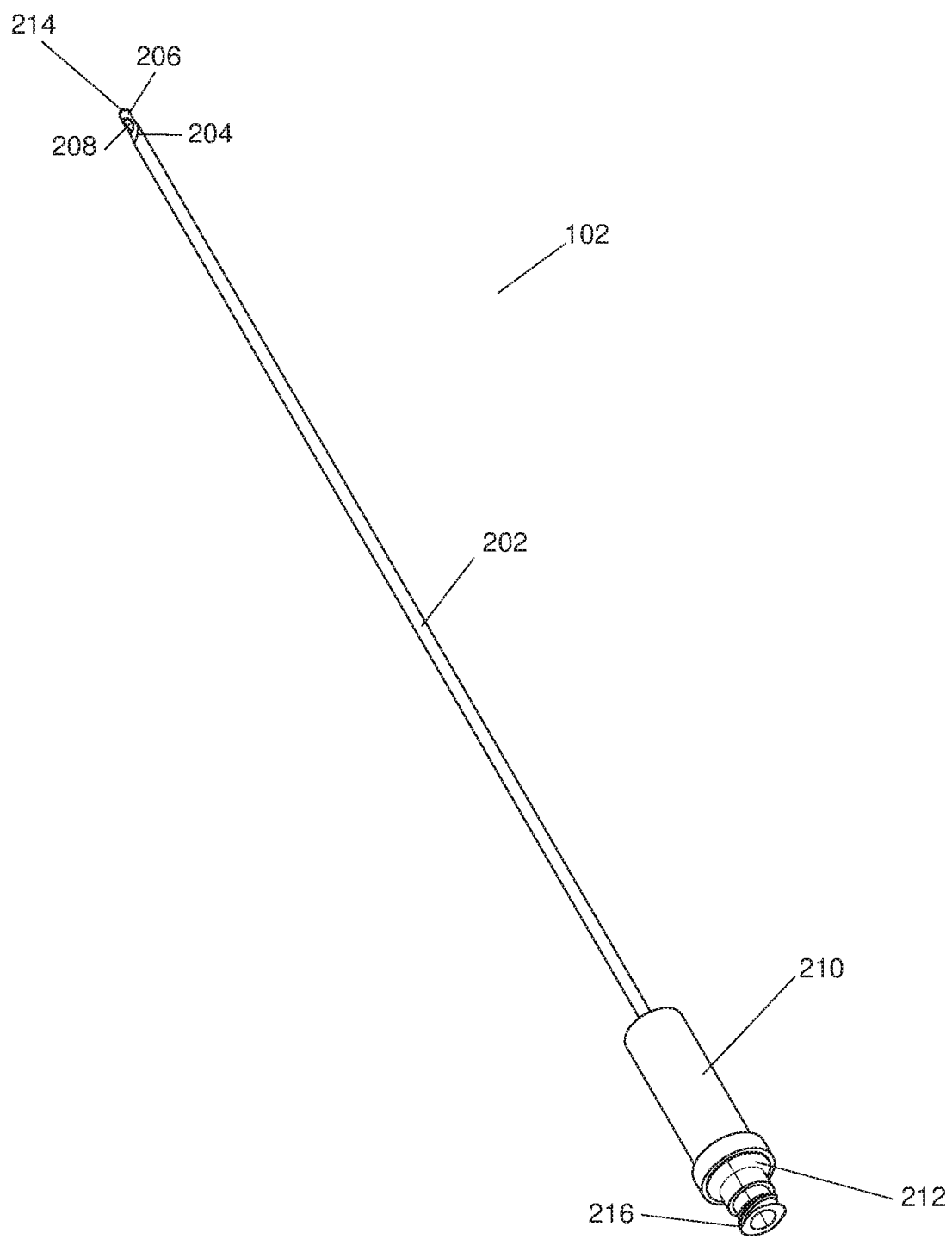
FIG. 2 illustrates a safety needle according to aspects of the present invention.

FIG. 2 illustrates a safety needle according to aspects of the present invention.

As shown in the figure, safety needle 102 includes cannula 202, cannula tip 204, stylet 206, stylet port 208, stylet tip 214, housing 210, hub 212, and connection means 216.

Cannula 202 is preferably constructed from a generally rigid material, such as metal or plastic, but other rigid materials may be considered. It may be extruded, welded, molded, or manufactured by any other method that would result in a generally rigid material. Cannula 202 is connected to hub 210 such that there is no relative movement between hub 210 and cannula 202. The connection may he via any mechanical means (a non-limiting example of which includes overmolding), adhesive means (a non-limiting example of which includes UV adhesive), or any other means that would create a bond between housing 210 and cannula 202 to prevent relative motion between the two components.

Cannula tip 204 is designed to penetrate through tissue, and therefore it is relatively sharp. Cannula tip 204 may be manufactured by any known means to create a beveled tip, a conical tip, a crown tip, or any other geometry that is known in the art to provide a tip sharp enough to penetrate tissue.

Stylet 206 is preferably constructed from a generally rigid material, such as metal or plastic, but other rigid materials may be considered. it may be extruded, welded, molded, or manufactured by any other method that would result in a generally rigid material. Stylet 206 is connected to housing 210 such that there may be relative motion between the two components. The outer diameter of stylet 206 is smaller than the inner diameter of cannula 202, and stylet 206 is slidably positioned inside of cannula 202.

Figure 6:
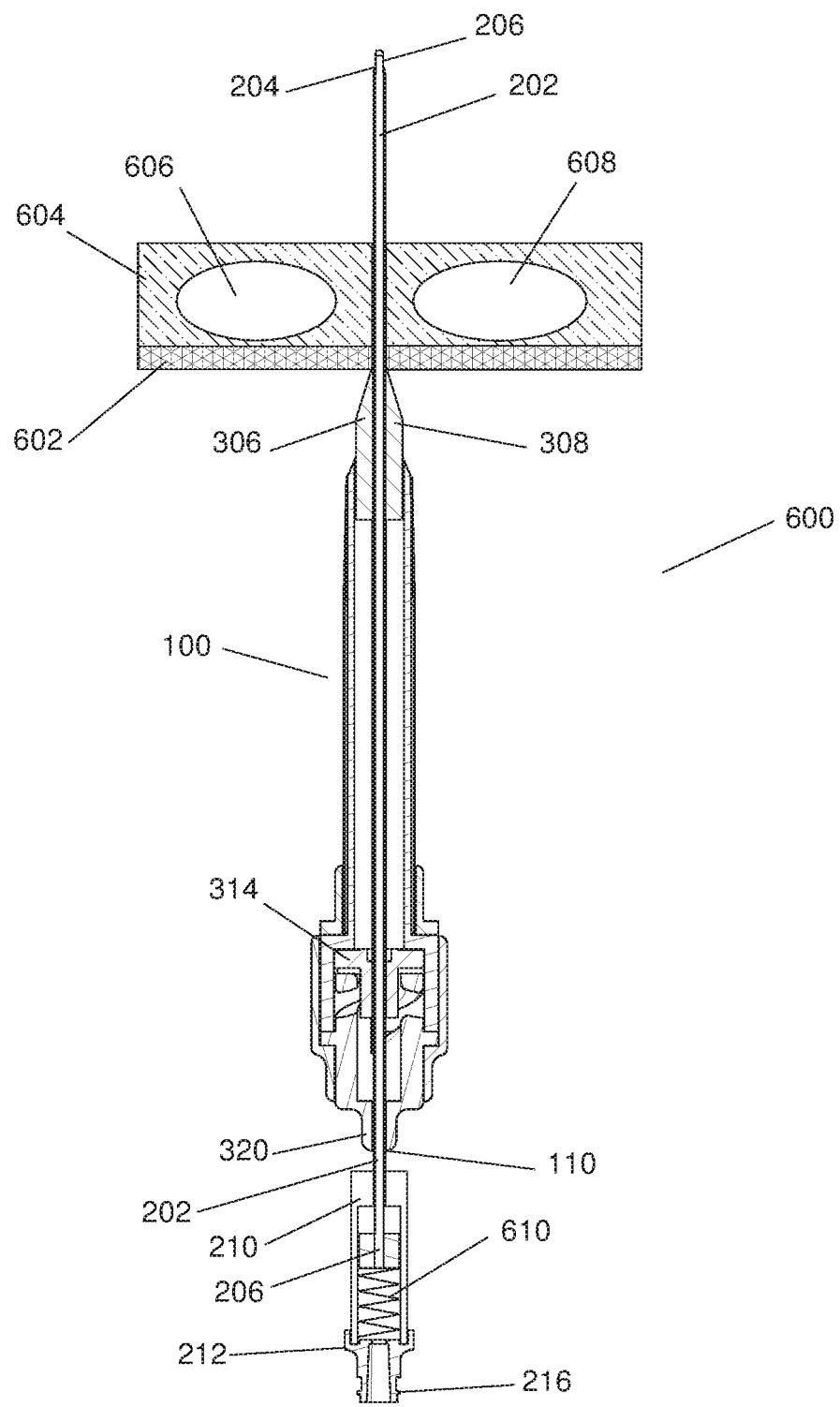
FIG. 6 illustrates a first step in inserting the insertion device according to aspects of the present invention.

Referring now to FIG. 6, housing 210 is a generally rigid component that is either machined or molded out of plastic. Housing 210 is connected to cannula 202 and to hub 212. The center of housing 21.0 is open to accommodate spring 610 and allow spring 610 to be compressed and uncompressed during use.

Stylet 206 is connected to spring 610 via any mechanical, chemical or adhesive means that would create a bond between the two components. in an alternate embodiment, stylet 206 and spring 610 may both be connected to an intermediate part, such that stylet 206 and spring 610 are effectively bonded together. Spring 610 is connected to housing 210 and hub 212 via any mechanical, chemical or adhesive means that would create a bond between the two components, In yet another alternate embodiment, spring 610 may freely float in between stylet 206 and hub 212 such that no bond between components is required.

Referring back to FIG. 2, stylet tip 214 is designed to avoid penetrating through tissue, and therefore it is relatively blunt and closed at the distal end. Stylet tip 214 may be manufactured by any known means to create a curved tip, a bullet tip, a flat tip, or any other geometry that is known in the art to create a closed distal tip that will avoid penetrating tissue.

Stylet port 208 is an open section in stylet 206 that is proximal to stylet tip 214 and distal to cannula tip 204 when spring 610 is uncompressed. Stylet port 208 may be manufactured by traditional grinding or machining techniques or by more advanced techniques, including electric discharge machining (EDM), chemical etching, or laser machining.

Referring back to FIG. 6, hub 212 is a generally rigid component that is either machined or molded out of plastic. Hub 212 is connected to spring 206 and to housing 210. Hub 212 includes connection means 216 such that hub 212 may be connected to an external source for fluid drainage or administration.

Referring back to FIG. 2, connection means 216 is shown as a threaded connection, however any suitable connection means (a non-limiting example of which includes a snap fit) that provide for connection of a fluid drainage or administration device is acceptable.

Referring to FIGS. 2 and 6, in operation, a user grasps hub 210 or another component that may be coupled to hub 210 and advances safety needle assembly 102 toward a patient's skin. The first component of safety needle assembly 102 that contacts the skin is stylet tip 214. As the user continues to push safety needle assembly 102 into the skin, the blunt stylet tip 214 transfers the pushing force through stylet 206, compresses spring 610, causes cannula 202 to move relative to stylet 206, and allows cannula tip 204 to move toward the skin.

When the pushing force is sufficient enough, cannula tip 204 will contact the skin and the sharp tip will penetrate the skin and soft tissues underneath the skin. When cannula tip 204 reaches an area of little or no resistance, spring 610 will uncompress, allowing stylet 206 to move forward again such that stylet tip 214 is distal to cannula tip 204, and stylet port 208 is exposed to the area. Areas of little or no resistance include fluid (or air) filled spaces such as the plerua, lungs, or any other fluid filled space the user desires to reach.

To confirm that safety needle assembly 102 is in the correct location, the user may connect a fluid drainage device to connection means 216 and use the fluid drainage device to pull fluid or air from the area as means of confirmation. Fluid drainage devices that may be used include syringes, suction canisters, wall suction, and any other means that may operate to pull fluid from the patient to confirm appropriate placement of safety needle assembly 102.

Figure 3:
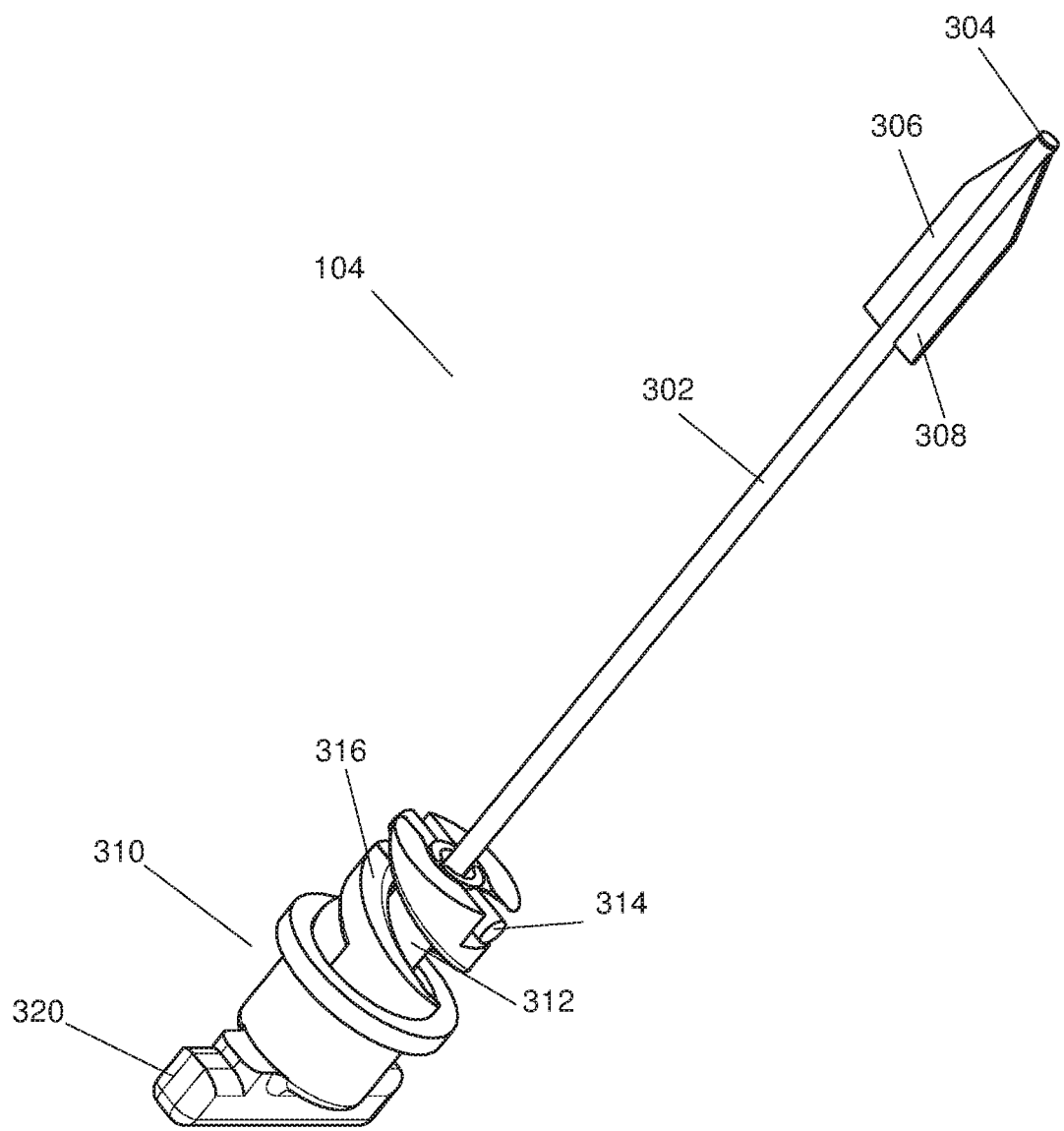
FIG. 3 illustrates a blade assembly according to aspects of the present invention.

FIG. 3 illustrates a blade assembly according to aspects of the present invention.

As shown in the figure, blade assembly 104 includes shaft 302, distal tip 304, blades 306 and 308, handle 310, follower shaft 312, and follower 314.

Shaft 302 is a rigid tube and is preferably made of metal, however any other rigid material would suffice. Shaft 302 is connected to follower shaft 314 such that there is no relative motion between the two components. The connection may be made via mechanical, adhesive, or chemical means. Shaft 302 is also connected to blades 306 and 308. The connection is preferably a welded connection, however other connection means may be employed. For example, shaft 302 may contain one or more slots at its distal end and blades 306 and 308 may contain one or more matching slots such that blades 306 and 308 may be assembled on to shaft 302 by sliding slotted sections of blades 306 and 308 on to the corresponding slots at the distal end of shaft 302.

Distal tip 304 is at the distal end of shaft 302 and is operable to provide a leading edge for blades 306 and 308. Distal tip 304 may be produced by any conventional tip grinding or finishing process, and it may be a beveled tip, a conical tip, a crown tip, or any other tip that would provide an appropriate leading edge for blades 306 and 308.

Blades 306 and 308 are preferably constructed from metal, more preferably from stainless steel, however any material suitable for medical applications would suffice. Blades 306 and 308 are operable to cut the skin of a patient, and as such are sufficiently sharp to cut skin. The specific shape, grind angles, and tip angles may be of any dimensions such that the effect of cutting skin may be accomplished. Blades 306 and 308 are attached to shaft 302 as previously described.

Handle 310 includes handle top 320 and cam 316. Handle 310 is preferably made of plastic via either machining or molding, however any other suitable materials or manufacturing methods may be used. Handle top 320 is designed to be gripped by a user in order to rotate handle 310 relative to follower shaft 312 and follower 314. Rotating handle top 320 and the motion of follower shaft 312 and follower 314 will be further discussed with reference to operation of blade assembly 104 below. Cam 316 is a slot within handle 310 in which follower 314 travels. Cam 316 may be constructed with any geometry that will provide the desired motion of follower 314.

Follower 314 and follower shaft 312 are both preferably made of plastic via either machining or molding, however any other suitable materials or manufacturing methods may be used. In some embodiments, follower 314 and follower shaft 312 may be a single component, however they are shown here as two separate components. Follower 314 and follower shaft 312 are bonded together by any suitable means that will effectively prevent relative motion between the two components. In addition, shaft 302 is bonded to follower 314 and follower shaft 312 to prevent relative motion between the three components.

In operation, a user will turn handle 310 to effect a linear movement of shaft 302. The user will grasp handle top 320 with one hand and dilator assembly 108 (not shown) with the other hand. Handle 310 therefore only rotates, and does not move in a linear direction when handle top 320 is turned. FIG. 3 shows blade assembly 104 with blades 306 and 308 fully deployed. To retract blades 306 and 308, the user would turn handle top 320 in the appropriate direction. Turning handle top 320 causes cam 316 to rotate. As cam 316 rotates, follower 314 moves in a linear manner such that follower 314 moves closer to handle top 320. To deploy blades 306 and 308, the user would turn handle top 320 in the opposite direction.

Figure 4:
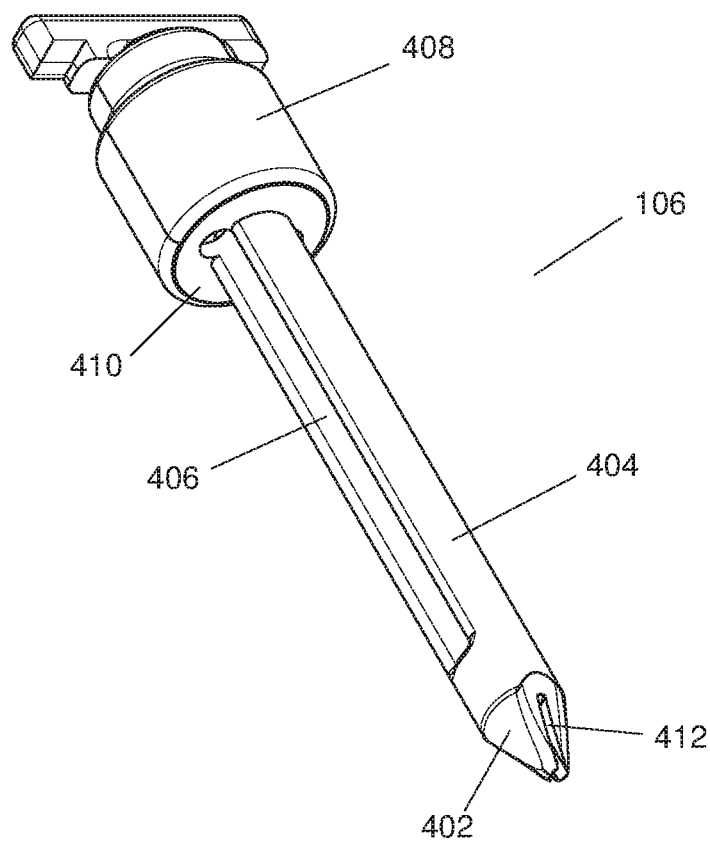
FIG. 4 illustrates an obturator assembly according to aspects of the present invention.

FIG. 4 illustrates an obturator assembly according to aspects of the present invention.

As shown in the figure, obturator assembly 106 includes obturator tip 402, obturator shaft 404, handle cover 408, and obturator hub 410. All components of obturator assembly 106 are preferably made from plastic via either machining or molding processes, however any suitable material or manufacturing method may be used to create the component.

Obturator tip 402 is operable to enlarge an opening in the skin, and includes blade slot 412. Blade slot 412 is operable to provide a pathway for blades 306 and 308 to be deployed beyond the distal-most portion of obturator tip 402 and to be fully retracted within obturator tip 402. Obturator tip 402 is connected to obturator shaft 404 by any suitable means that would prevent relative motion between the two components, in an alternate embodiment, obturator tip 402 and obturator shaft 404 may be a single component.

Obturator shaft 404 is operable to travel within the enlarged opening created by obturator tip 402, and includes obturator slot 406. Obturator slot 406 is present to reduce weight and manufacturing costs. in an alternate embodiment, obturator slot 406 may be omitted entirely such that obturator shaft 404 is a continuous tube with no openings in its diameter.

Obturator hub 410 is connected to obturator shaft 404 by any means that would create a bond to prevent relative motion between the two components. Obturator hub 410 is operable to constrain the linear motion of follower 314 (not shown), such that blades 306 and 308 can only extend from obturator tip 402 by a defined distance.

Handle cover 408 is operable to attach to obturator hub 410 and cover cam 316 (not shown) such that a user cannot interfere with the operation of cam 316. Handle cover 408 may be a single component or multiple components that can be attached together. Additionally, in an alternate embodiment, handle cover 408 and obturator hub 410 may be a single component.

Returning to FIG. 1, and with reference to FIGS. 2-4, assembly of insertion device 100 will be described.

To assemble insertion device 100, safety needle 102 is inserted through handle hole 110 and extends through the inner diameter of shaft 302 of blade assembly 104, extending beyond distal tip 304. The combination of safety needle 102 and blade assembly 104 is inserted through the inner diameter of obturator shaft 404 until obturator hub 410 contacts cam 316 of blade assembly 104. Handle cover 408 is then installed to cover cam 316. Finally, the entire assembly is inserted through the inner diameter of dilator assembly 108 to complete the assembly process. There are no connections between dilator assembly 108 and the rest of the components; a simple press-fit interaction serves to keep dilator assembly 108 connected to the rest of the components. In an alternate embodiment, dilator assembly 108 may detachably lock to obturator assembly 106. Dilator assembly 108 will be further described with reference to FIGS. 6-8.

Figures 5A, 5B:
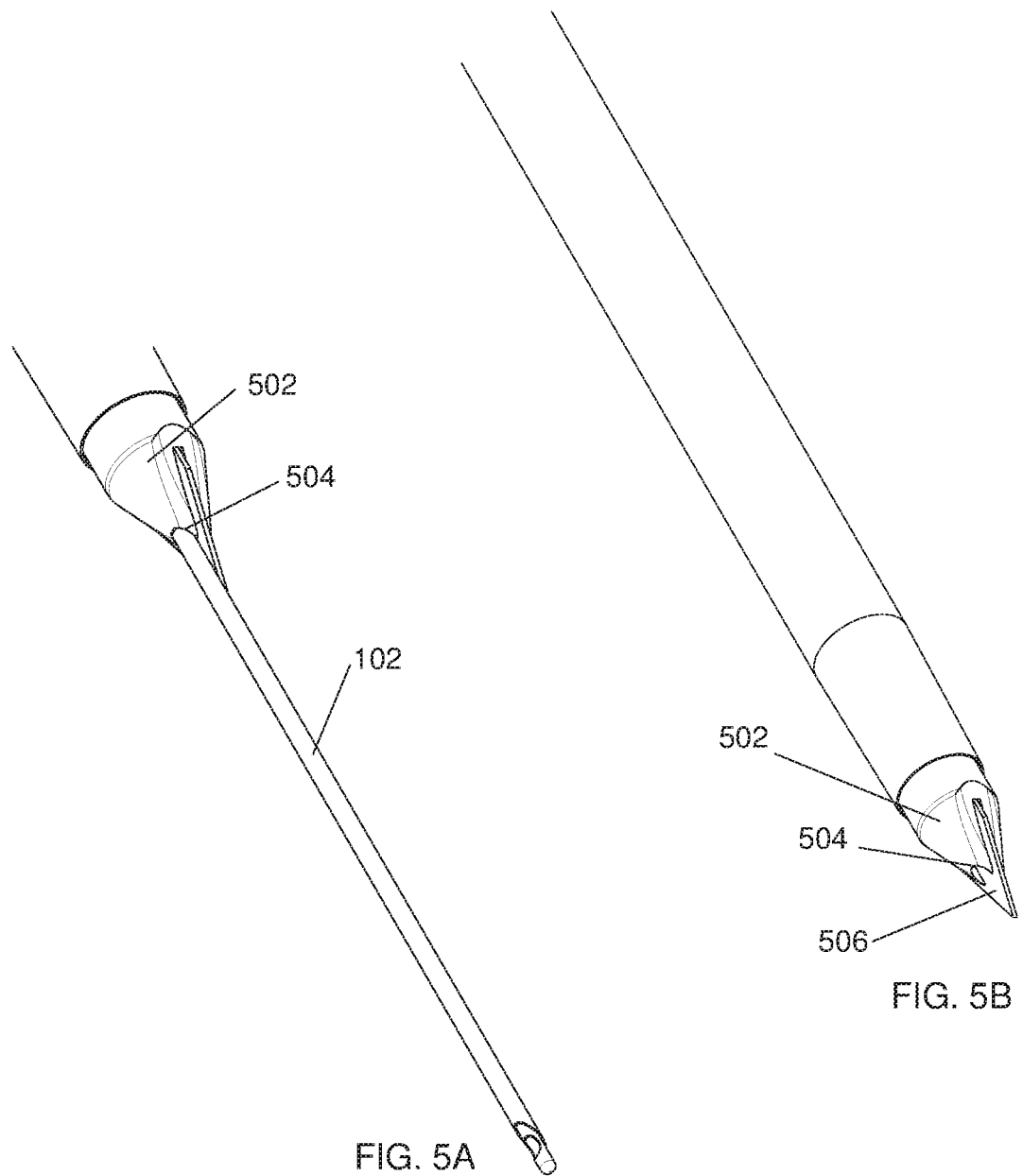
FIGS. 5A-B illustrate an alternate embodiment of a blade assembly and an obturator assembly according to aspects of the present invention.

FIGS. 5A-B illustrate an alternate embodiment of a blade assembly and an obturator assembly according to aspects of the present invention.

As shown in the figures, obturator tip 502 includes cutout 504 to accommodate safety needle 102. A blade slot similar to blade slot 412 provides space for blade 506 to deploy and retract.

In this embodiment, blade 506 is a single blade instead of multiple blades as previously described. The single blade may be attached to shaft 302 by any means previously described. If attaching multiple blades to the outer diameter of shaft 302 is difficult to accomplish, this alternate embodiment may be employed, as methods to attach a single blade to a shaft are well known in the art.

In attaching blade 506 to shaft 302, a difficulty is encountered as safety needle 102 and blade 506 cannot be longitudinally coaxial with each other as is possible with the multiple blade design. Therefore, it is necessary to create cutout 504 to accommodate safety needle assembly 102. In this embodiment, blade 506 slides along the outer diameter of safety needle assembly 102.

Testing has proven that, even though safety needle 102 is not concentric with respect to the rest of insertion device 100, the ability of blade 506 to enlarge the pathway created by safety needle 102 is not impacted, and the performance of insertion device 100 is not diminished.

In yet another alternate embodiment, and with further reference to FIGS. 3-4, it may be desirable to eliminate the need to turn handle 320 to deploy and retract blades 306 and 308. In such an embodiment, blade assembly 104 may contact a spring that rests on obturator hub 410. There may be a window in handle cover 408 such that the user's finger could reach blade assembly 104 through the window. Access to blade assembly 104 may also be available via obturator slot 406. When the user desires to deploy the blades, the user would extend a finger into the window and press down on blade assembly 104, compressing the spring and exposing the blades. After using the blades, the user would remove his/her finger from blade assembly 104, which would then automatically retract blades 306 and 308 into obturator assembly 106 as the spring uncompressed.

FIG. 6 illustrates a first step in inserting the insertion device according to aspects of the present invention.

As shown in the figure, system 600 includes skin 602, soft tissue 604, and ribs 606 and 608.

Figure 7:
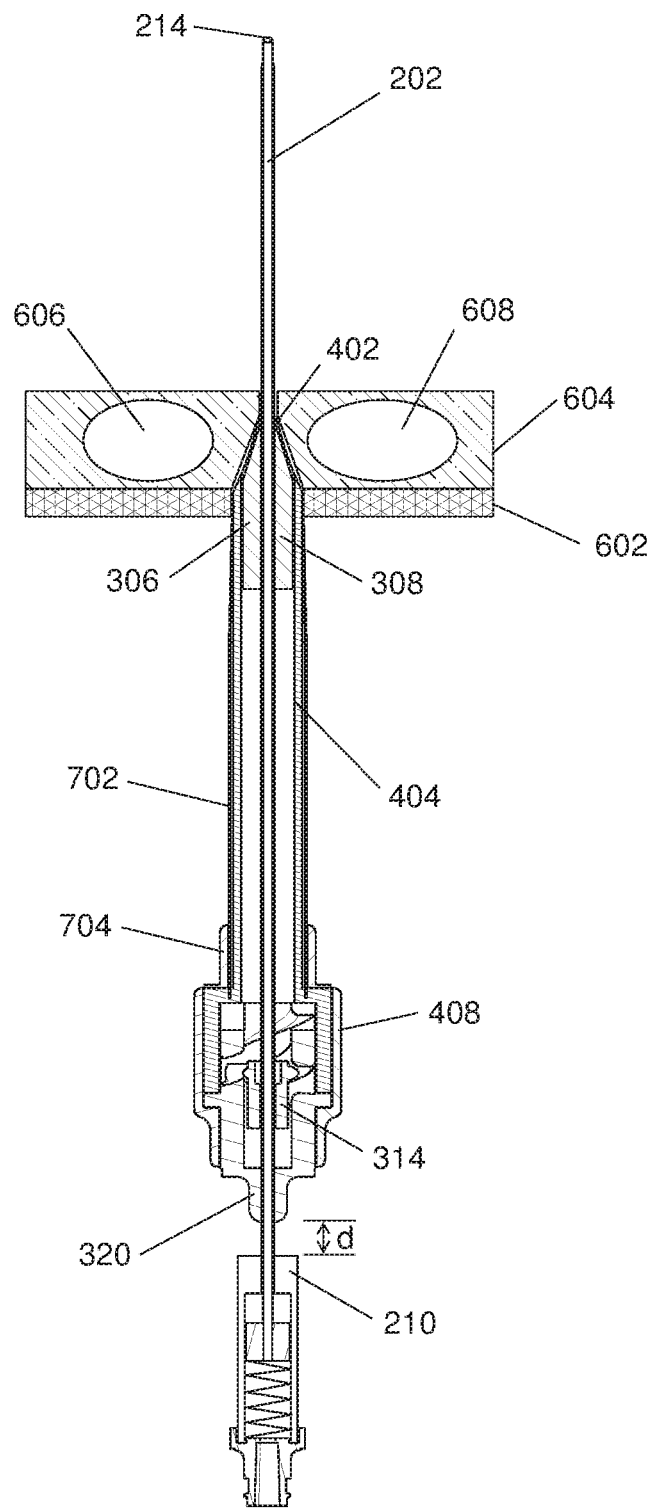
FIG. 7 illustrates a second step in inserting the insertion device according to aspects of the present invention.

Prior to inserting device 100 into a patient, a user will palpate the skin to determine the appropriate insertion point between ribs 606 and 608. Once the desired location is found, the user begins to insert insertion device 100. While not shown in FIG. 6, when first inserting insertion device into the patient, blades 306 and 308 are not deployed and are located within obturator assembly 106 (similar to the device as shown in FIG. 7).

When inserting insertion device 100 into the patient, safety needle 102 is the first component to contact the patient's skin 602. As described with reference to FIG. 2, pushing safety needle 102 against the patient's skin 602 causes stylet 206 to retract, exposing the sharp cannula tip 204 to the skin. As the user continues to push, cannula tip 204 cuts through skin 602 and soft tissue 604. Soft tissue 604 may include muscle, fat, fascia, or any other soft tissues with which safety needle 102 may come in contact with during the procedure.

A skilled user can generally tell when the desired location is reached, as a distinct decrease in resistance occurs. The decrease in resistance is an indication that safety needle 102 has reached the desired, fluid-filled location. To confirm that safety needle 102 has reached the desired location, the user will attach a fluid drainage device to hub 212 via connection means 216. The user will then attempt to drain fluid from the area. If the desired fluid is drawn from the area, the user may continue with the procedure. If the desired fluid is not drawn from the area, the user may need to continue in attempts to find the desired location.

Assuming the desired fluid has been located, the user then deploys blades 306 and 308 by turning handle 320 until handle 320 cannot be turned any more, meaning blades 306 and 308 are fully deployed. The user then advances insertion device 100 until blades 306 and 308 enter skin 602 to create a skin nick. If desirable, after creating the skin nick, the user may pull insertion device back such that blades 306 and 308 are not in skin 602, rotate insertion device 100 90 degrees, and then advance insertion device again until blades 306 and 308 enter skin 602. After one or more skin nicks are created, the user turns handle 320 in the opposite direction until it cannot be turned any more, meaning blades 306 and 308 are fully retracted. The user can then further advance insertion device 100, which is further described with reference to FIG. 7.

In an alternate method, the user may deploy blades 306 and 308 first, create a skin nick, and then retract blades 306 and 308. The user may then proceed with inserting safety needle 102 into the patient as previously described, or the user may decide to forego using safety needle 102 and instead insert obturator assembly 106, blade assembly 104, and dilator assembly 108 into the desired space within the patient.

FIG. 7 illustrates a second step in inserting the insertion device according to aspects of the present invention.

As shown in the figure, insertion device 100 is pushed further into the patient. As insertion device 100 advances, obturator tip 402 expands the pathway created by safety needle 102 and the one or more skin nicks. The user holds safety needle 102 with one hand while advancing obturator assembly 106, blade assembly 104, and dilator assembly 108. The distance between housing 210 and handle 320, noted as "d", will increase as the user continues to advance obturator assembly 106, blade assembly 104, and dilator assembly 108.

When obturator tip 402 reaches stylet tip 214, the user may stop advancement. The user may use an appropriate imaging technique to determine when obturator tip 402 reaches stylet tip 214. In an alternate embodiment, cannula 202 may include an indicator mark, such that when handle 320 no longer covers the indicator mark, obturator tip 402 has reached stylet tip 214.

The user can then remove components to prepare the patient for insertion of a catheter. Safety needle assembly 102, blade assembly 104, and obturator assembly 106 may all be removed from dilator assembly 108 at the same time. To remove the components, the user will grip dilator shaft 702 with one hand and handle cover 408 with the other hand. Dilator shaft 702 will be further described with reference to FIG. 8. While holding dilator shaft 702 steady, the user will pull back on handle cover 408. This will serve to detach Safety needle assembly 102, blade assembly 104, and obturator assembly 106 from the press-fit connection to dilator assembly 108. As the user continues to pull back on handle cover 408, all components will be removed from dilator assembly 108, leaving dilator assembly 108 in the body.

Figure 8:
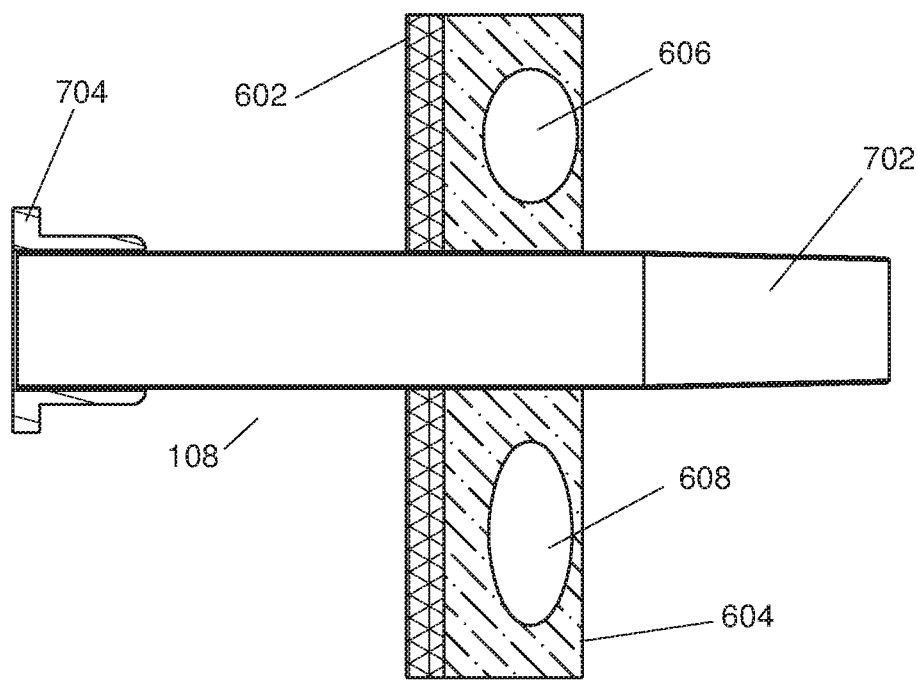
FIG. 8 illustrates a final step in inserting the insertion device according to aspects of the present invention.

FIG. 8 illustrates a final step in inserting the insertion device according to aspects of the present invention.

As shown in the figure, dilator assembly 108 is in the patient. Dilator assembly 108 includes dilator shaft 702 and dilator hub 704. Dilator shaft 702 is preferably made of plastic and may be extruded, molded, or manufactured in any other known way to create the desired geometry. Dilator hub 704 is also preferably made of plastic by any known method to create the desired geometry. Dilator hub 704 and dilator shaft 702 are connected by any known methods that would serve to prevent any relative motion between the two components.

At this point in the procedure, the user will typically place a catheter through the lumen of dilator shaft 702 to reach the desired location within the body. Essentially, dilator shaft 702 is simply a conduit through which another device (i.e., a catheter) is placed. Once the catheter is placed in the desired location, dilator assembly 108 is removed from the patient. The user then completes the procedure by closing skin 602 around the catheter.

Figure 9:
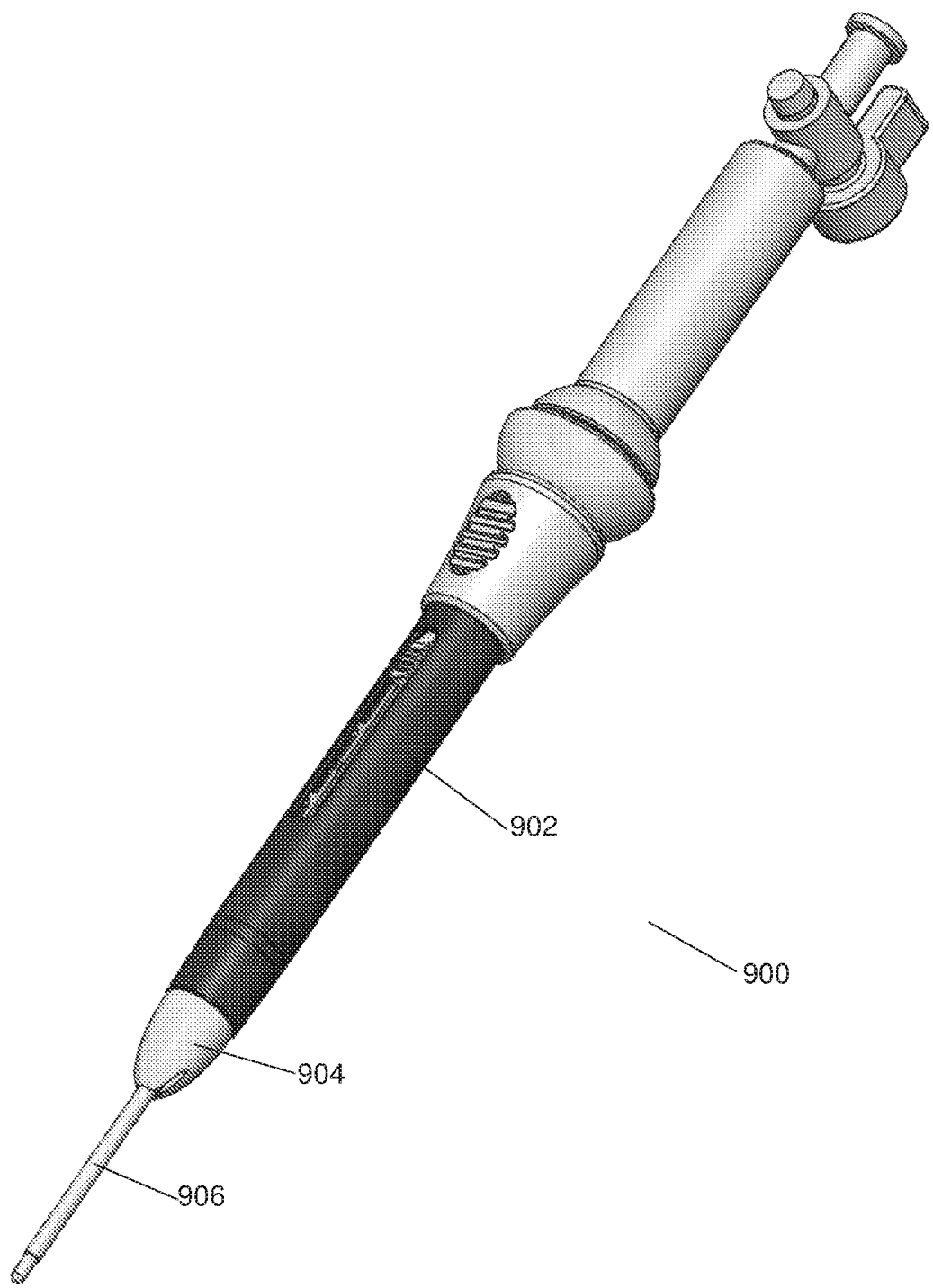
FIGS. 9-10 illustrate an alternate embodiment of an insertion device according to aspects of the present invention.
Figure 10:
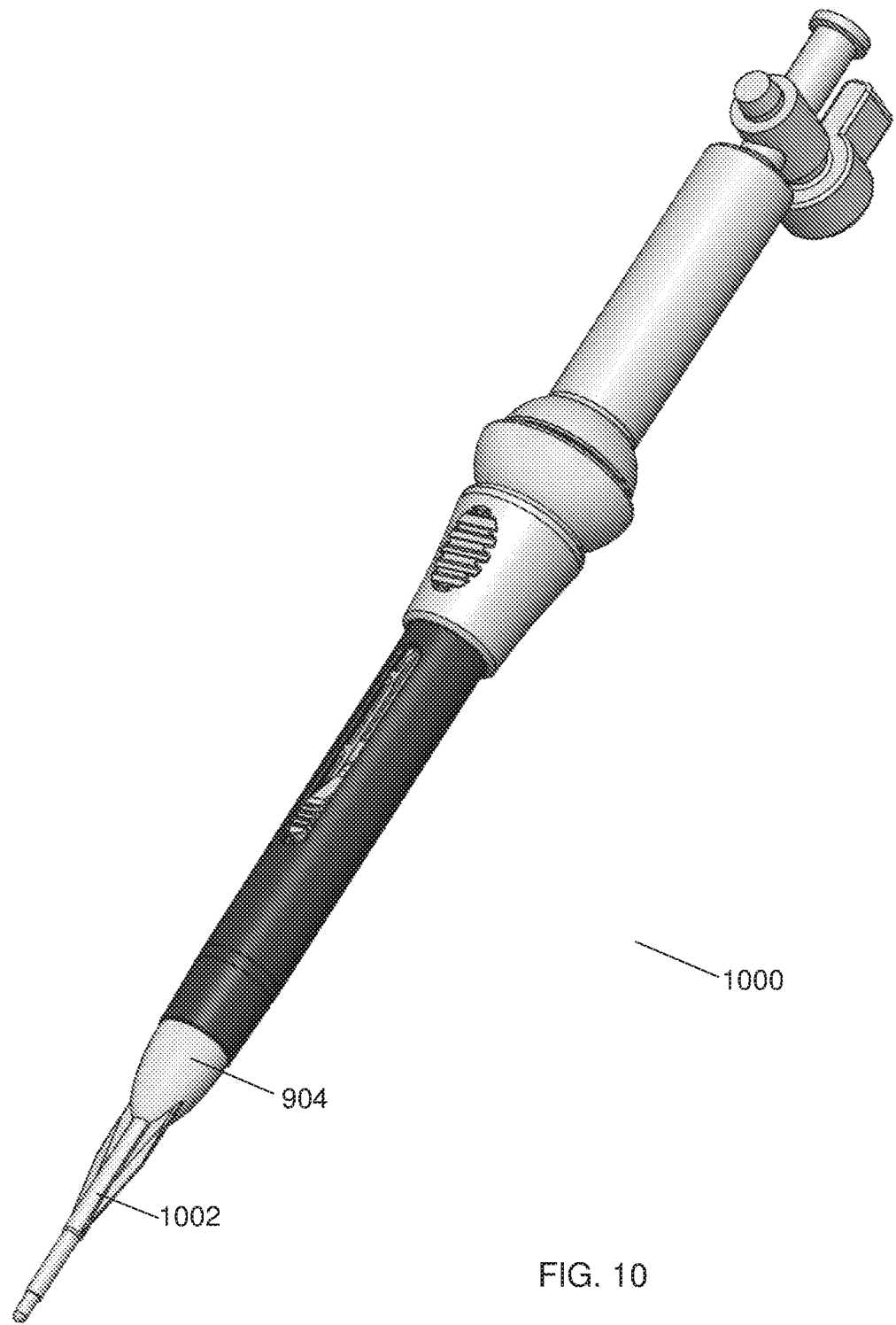

FIGS. 9-10 illustrate an alternate embodiment of an insertion device according to aspects of the present invention. As shown in FIG. 9, insertion device 900 includes dilator assembly 902, obturator assembly 904, and safety needle assembly 906. As shown in FIG. 10, insertion device 1000 includes blade assembly 1002.

Specific aspects of dilator assembly 902, obturator assembly 904, safety needle assembly 906, and blade assembly 1002 will be further described with reference to FIGS. 11-14.

Figure 11:
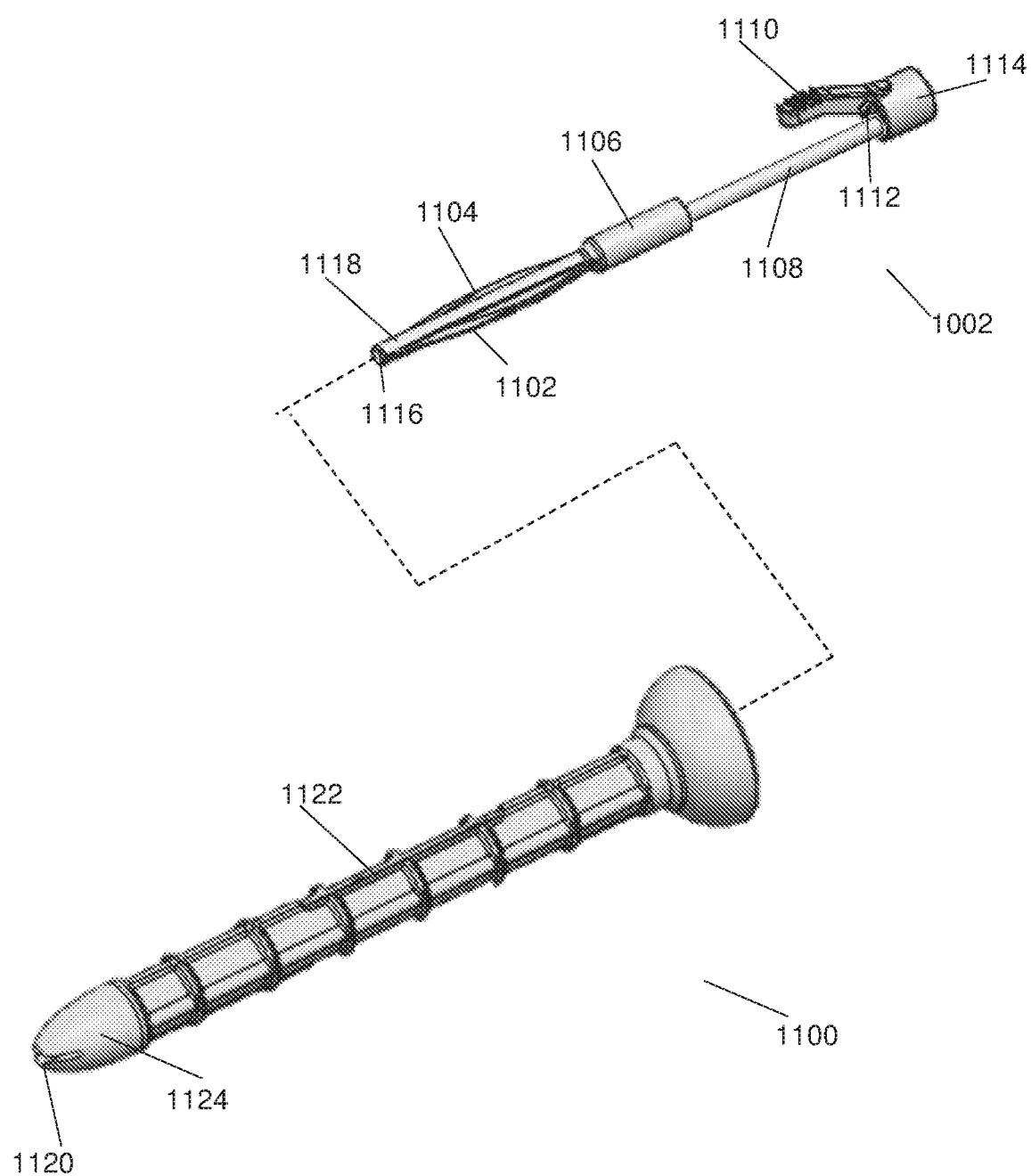
FIG. 11 illustrates the process by which an obturator assembly is assembled for an alternate embodiment of the insertion device.

FIG. 11 illustrates the process by which an obturator assembly is assembled for an alternate embodiment of the insertion device.

As shown in the figure, blade assembly 1002 includes blades 1102 and 1104, blade tube 1106, extension tube 1108, button 1110, lock 1112, cap 1114, lumen 1116, and shaft 1118. Obturator blank 1100 includes obturator tip 1124, blade slot 1120, and button slot 1122.

Shaft 1118 is a rigid tube and is preferably made of metal, however any other rigid material would suffice. Shaft 1118 is connected to blade tube 1106 such that there is no relative motion between the two components. The connection may be made via mechanical, adhesive, or chemical means. Shaft 1118 is also connected to blades 1102 and 1104. The connection is preferably a welded connection, however other connection means may be employed. As a non-limiting example, shaft 1118 may contain one or more slots at its distal end and blades 1102 and 1104 may contain one or more matching slots such that blades 1102 and 1104 may be assembled on to shaft 1118 by sliding slotted sections of blades 1102 and 1104 on to the corresponding slots at the distal end of shaft 302.

Blades 1102 and 1104 are preferably constructed from metal, more preferably from stainless steel, however any material suitable for medical applications would suffice. Blades 1102 and 1104 are operable to cut the skin of a patient, and as such are sufficiently sharp to cut skin. The specific shape, grind angles, and tip angles may be of any dimensions such that the effect of cutting skin may be accomplished. Blades 1102 and 1104 are attached to shaft 1118 as previously described, Blade tube 1106 is a rigid tube and is preferably made of metal, however any other rigid material would suffice. Blade tube 1106 is connected to shaft 1118 as previously described, and blade tube 1106 is also connected to extension tube 1108 such that there is no relative motion between the two components. The connection may be made via mechanical, adhesive, or chemical means.

Extension tube 1108 is a rigid tube and is preferably made of metal, however any other rigid material would suffice. Extension tube 1108 is connected to blade tube 1106 as previously described, and extension tube 1108 is also connected to cap 1114 such that there is no relative motion between the two components. The connection may be made via mechanical, adhesive, or chemical means.

Cap 1114 is a rigid body and is preferably made of metal, however any other rigid material would suffice. Cap 1114 is operable to connect to extension tube 108 and to connect to button 1110.

Button 1110 is a deflectable body and is preferably made of any resilient material that can be deflected and then return to its original position. Button 1110 is connected to cap 1114 as previously described. Button 1110 also includes lock 1112, which protrudes from the side of button 1110 and is operable to secure blade assembly 1002 in a specific location. The operation of button 1110, lock 1112, and blade assembly 1002 will be further described with reference to FIG. 1344.

The individual components of blade assembly 1002 may all be manufactured separately and connected together as described above, but in alternate embodiments blade assembly 1002 may be a single, continuous component. In other alternate embodiments, various combinations of the individual components may be combined into single components for ease of manufacturing.

Obturator blank 1100 is preferably made from plastic via either machining or molding processes, however any suitable material or manufacturing method may be used to create the component. Obturator tip 1124 is operable to enlarge an opening in the skin, and includes blade slot 1120. Blade slot 1120 is operable to provide a pathway for blades 1102 and 1104 to be deployed beyond the distal-most portion of obturator tip 1124 and to be fully retracted within obturator tip 1124.

Button slot 1122 is an opening within the shaft of obturator blank 1100, and it is operable to provide an opening in which button 1110 may travel. The operation of button 1110 and its interaction with button slot 1122 will be further described with reference to FIG. 1344.

In operation, blade assembly 1002 is inserted into obturator blank 1100 to create obturator assembly 904. In some embodiments, obturator blank 1100 is created by molding 2 halves of the component that are not attached. The 2 halves may then be assembled around blade assembly 1002 before being connected by mechanical or chemical means.

Figure 12:
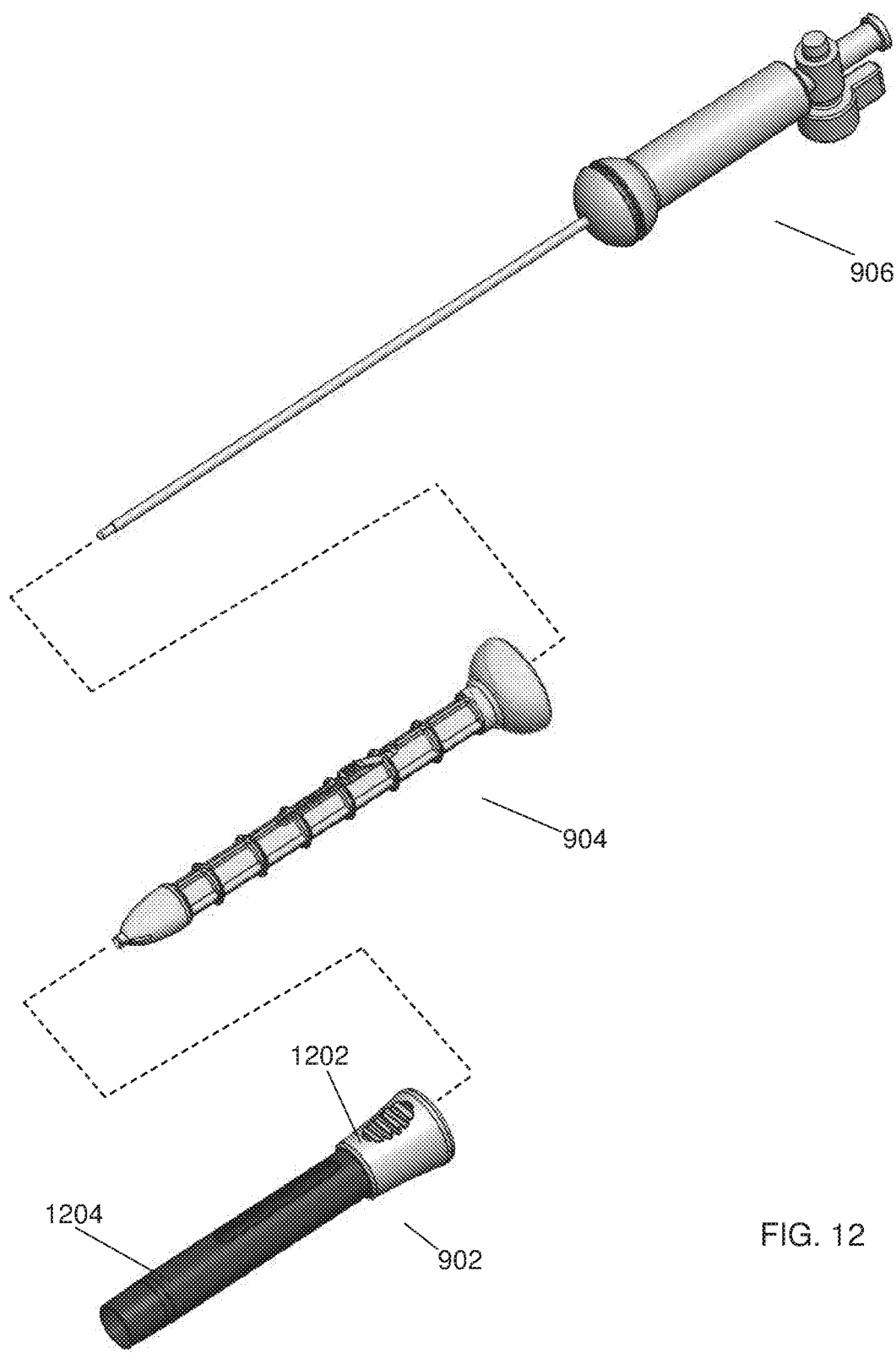
FIG. 12 illustrates the assembly process to create an alternate embodiment of the insertion device.

FIG. 12 illustrates the assembly process to create an alternate embodiment of the insertion device.

As shown in the figure, safety needle assembly 906 is inserted through obturator assembly 904. More specifically, safety needle assembly 906 is inserted through blade assembly 1002, which is part of obturator assembly 904. Safety needle assembly 906 is substantially similar in construction and operation to safety needle 102 from FIGS. 2, 6, and 7. Safety needle assembly 906 is releasably attached to obturator assembly 904 such that the components can be easily attached and detached. In some embodiments, and as a non-limiting example, there may be a tongue-in-groove connection between the two components such that a nominal amount of force is required to connect and disconnect, however in other embodiments there are no additional mechanisms to secure the components together.

The combination of safety needle assembly 906 and obturator assembly 904 is then inserted through dilator assembly 902. Dilator assembly 902 includes dilator shaft 1204 and dilator hub 1202. Dilator shaft 1204 is preferably made of plastic and may be extruded, molded, or manufactured in any other known way to create the desired geometry. Dilator hub 1202 is also preferably made of plastic by any known method to create the desired geometry. Dilator hub 1202 and dilator shaft 1204 are connected by any known methods that would serve to prevent any relative motion between the two components.

Obturator assembly 904 is releasably attached to dilator assembly 902 such that the components can be easily attached and detached. In some embodiments, and as a non-limiting example, there may be a tongue-in-groove connection between the two components such that a nominal amount of force is required to connect and disconnect, however in other embodiments there are no additional mechanisms to secure the components together.

Figure 13:
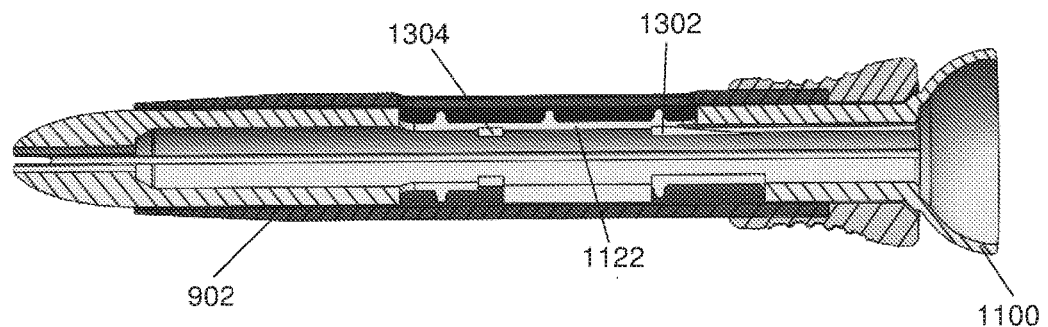
FIG. 13 illustrates a cross section of a dilator and an obturator of an alternate embodiment of the insertion device.

FIG. 13 illustrates a cross section of a dilator and an obturator of an alternate embodiment of the insertion device.

As shown in the figure, the cross section shows obturator blank 1100 assembled with dilator assembly 902. Obturator blank 1100 includes slots 1302 and 1304. Slots 1302 and 1304 are operable to mate with lock 1112 of blade assembly 1002.

Figure 14:
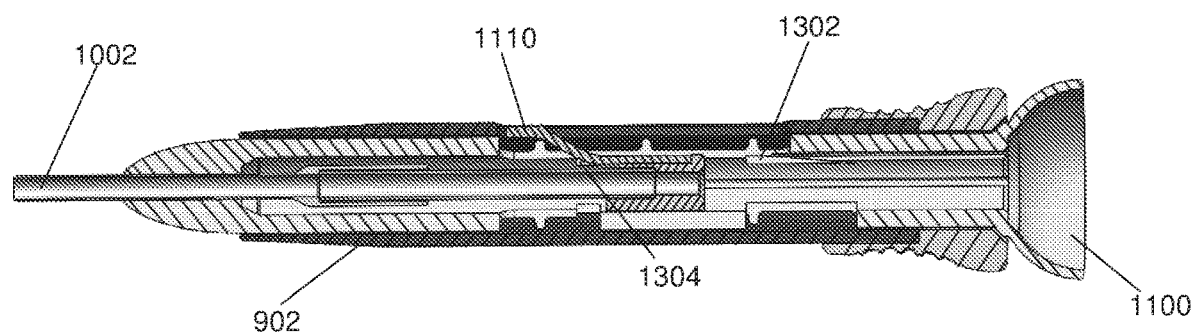
FIG. 14 illustrates a cross section of a dilator, obturator, and blade assembly of an alternate embodiment of the insertion device.

FIG. 14 illustrates a cross section of a dilator, obturator, and blade assembly of an alternate embodiment of the insertion device.

As shown in the figure, the cross section shows an assembly of obturator blank 1100, dilator assembly 902, and blade assembly 1002. Lock 1112 (not shown) is engaged with slot 1304, locking blade assembly 1002 in place. If the user desires to move blade assembly 1002, the user would deflect button 1110 (typically using finger pressure) to disengage lock 1112 from slot 1304. Then, keeping pressure on button 1110 to maintain it in the deflected position, the user would pull button 1110 back towards slot 1302 until slot 1302 engaged with lock 1112, thus locking blade assembly 1002 in a different position.

Operation of the device during a medical procedure will now be described with reference to FIGS. 9, 10, and 14. In a medical procedure, the user will receive the device with blades 1104 and 1102 in the retraced position, where lock 1112 is engaged with slot 1302. At this point, the only component protruding through obturator assembly 904 is safety needle assembly 906. After the doctor determines the appropriate place to insert the device, safety needle assembly 906 is inserted to the desired location in a manner similar to that described with reference to FIG. 6 and safety needle 102.

In order to create a larger incision in which dilator assembly 902 can fit, the user then depresses button 1110, disengaging lock 1112 from slot 1302. The user then advances button 1110 toward the distal end of the device, causing blade assembly 1002 to advance. When lock 1112 engages with slot 1304 the user releases button 1110, locking blade assembly 1002 in place, exposing blades 1102 and 1104. The user then advances the device until blades 1102 and 1104 enter the skin to create a skin nick. If desirable, after creating the first skin nick, the user may choose to pull the device back until blades 1102 and 1104 are not in the skin, rotate the device 90 degrees, and then advance the device again until blades 1102 and 1104 enter the skin again to create a second skin nick.

After the user creates the desired skin nicks, the user depresses button 1110, disengaging lock 1112 from slot 1304. The user then retracts button 1110 toward the proximal end of the device, causing blade assembly 1002 to retract, fully retracting blades 1102 and 1104 inside the device.

An advantage of this configuration is that it provides the ability of the user to actuate the blades with one hand, making the procedure more convenient compared to procedures performed with trocars requiring two hands to operate.

As described with reference to FIG. 7, the user will then advance obturator assembly 904 and dilator assembly 902 further into the patient while holding safety needle assembly 906 to prevent it from moving further into the patient. When the tip of obturator assembly 904 reaches the tip of safety needle assembly 906, the user may stop advancing the combination of obturator assembly 904 and dilator assembly 902. The user may use an appropriate imaging technique to determine when obturator tip 1124 reaches the tip of safety needle assembly 906. In an alternate embodiment, markers on the device may indicate when obturator tip 1124 reaches the tip of safety needle assembly 906, eliminating the need to use an imaging technique.

The user can then remove components to prepare the patient for insertion of a catheter. Safety needle assembly 906 and obturator assembly 904 may be removed from dilator assembly 902 at the same time, or separately as the user desires. To remove the components at the same time, the user would grip dilator assembly 902 with one hand and obturator assembly 904 with the other, and simply hold dilator assembly 902 still while pulling obturator assembly 904 until only dilatory assembly 902 is left in the patient. Alternatively, the user may first remove safety needle assembly 906, then remove obturator assembly 904.

As discussed with reference to FIG. 8, at this time, only dilator assembly is left in the patient, and the user will typically place a catheter through the lumen of the dilator shaft 1204 to reach the desired location in the body. Once the catheter is in the desired location, dilator assembly 902 is removed from the patient, and the user completes the procedure by closing the skin around the catheter.

Figure 15:
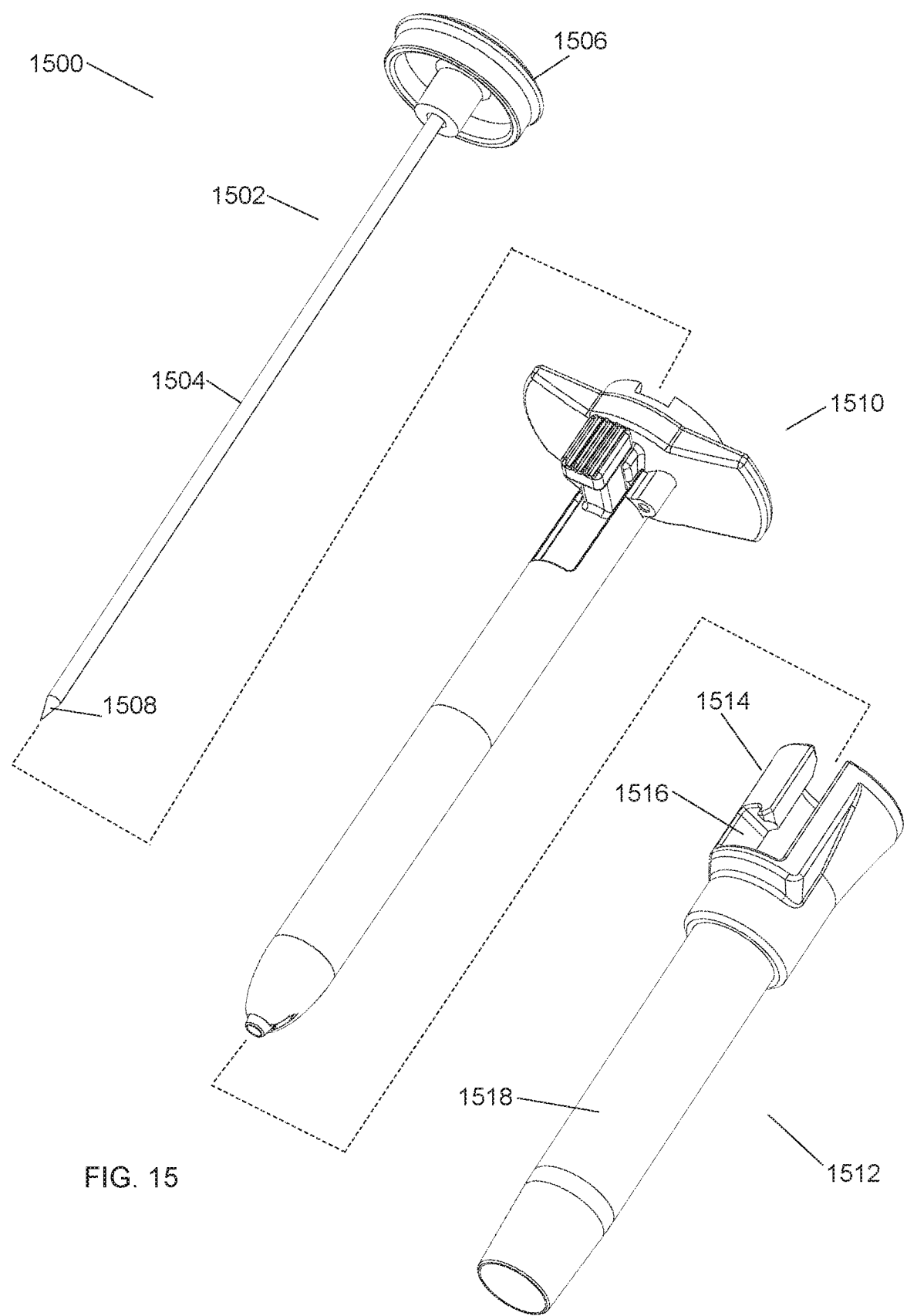
FIG. 15 illustrates another alternate embodiment of an insertion device according to aspects of the present invention.

FIG. 15 illustrates another alternate embodiment of an insertion device according to aspects of the present invention.

As shown in the figure, insertion device 1500 includes stylet assembly 1502, obturator assembly 1510, and dilator assembly 1512. Stylet assembly 1502 further includes stylet body 1504, stylet top 1506, and stylet tip 1508. Dilator assembly 1512 further includes dilator top 1514, dilator slot 1516, and dilator body 1518.

Stylet body 1504 is a rigid rod and is preferably made of metal, however any other rigid material would suffice. Stylet body 1504 may have a circular cross-section, however other cross-sectional shapes may be used, and stylet body 1504 is sized and configured to fit within a blade assembly that will be further described with reference to FIG. 16. Stylet body 1504 is connected to stylet top 1506 such that there is no relative motion between the two components. The connection may be made by any conventional mechanical, adhesive, or chemical connection methods or processes. Stylet top 1506 provides a surface for a user to push when using insertion device 1500, therefore any shape that provides a suitable pushing surface may be used. Stylet top 1506 is generally rigid, and is preferably made from molded plastic, however any other rigid materials may be used. Stylet tip 1508 is the distal end of stylet body 1504, and is sharpened such that it can penetrate skin and underlying tissues. Stylet tip 1508 may be manufactured with a conical tip, a serrated tip, a beveled tip, or any other tip configuration that is able to puncture skin to enter the body.

In an alternate embodiment, stylet body 1504 may be hollow, stylet tip 1508 may include one or more openings, and stylet top 1506 may include an aspiration connection such that the user may connect an aspiration device to stylet top 1506 and aspirate fluid through stylet tip 1508 and stylet body 1504. The one or more openings within stylet tip 1508 may be at the distal end of stylet tip 1508, but they may also be in other locations on stylet tip 1508. There may also be additional openings along stylet body 1504 if desired to provide additional fluid pathways for aspiration.

Dilator top 1514 is preferably made of plastic and may be extruded, molded, or manufactured in any other known way to create the desired geometry. Dilator slot 1516 is an open space in the wall of dilator top 1514 that allows for a pushrod to travel within and along dilator slot 1516. The pushrod will be further described with reference to FIG. 16. Dilator body 1518 is also preferably made of plastic and may be extruded, molded, or manufactured in any other known way to create the desired geometry.

Stylet assembly 1502 is sized and configured to fit within obturator assembly 1510 until stylet tip 1508 extends beyond the distal end of obturator assembly 1510. Obturator assembly 1510 is sized and configured to fit within dilator assembly 1512 until the distal end of obturator assembly 1510 extends beyond the distal end of dilator assembly 1512. To assemble insertion device 1500, stylet assembly 1502 is first releasably connected to obturator assembly 1510, and then the combination of stylet assembly 1502 and obturator assembly 1510 is releasably connected to dilator assembly 1512. The fully assembled insertion device will be shown and further described with reference to FIGS. 19A-D.

Figure 16:
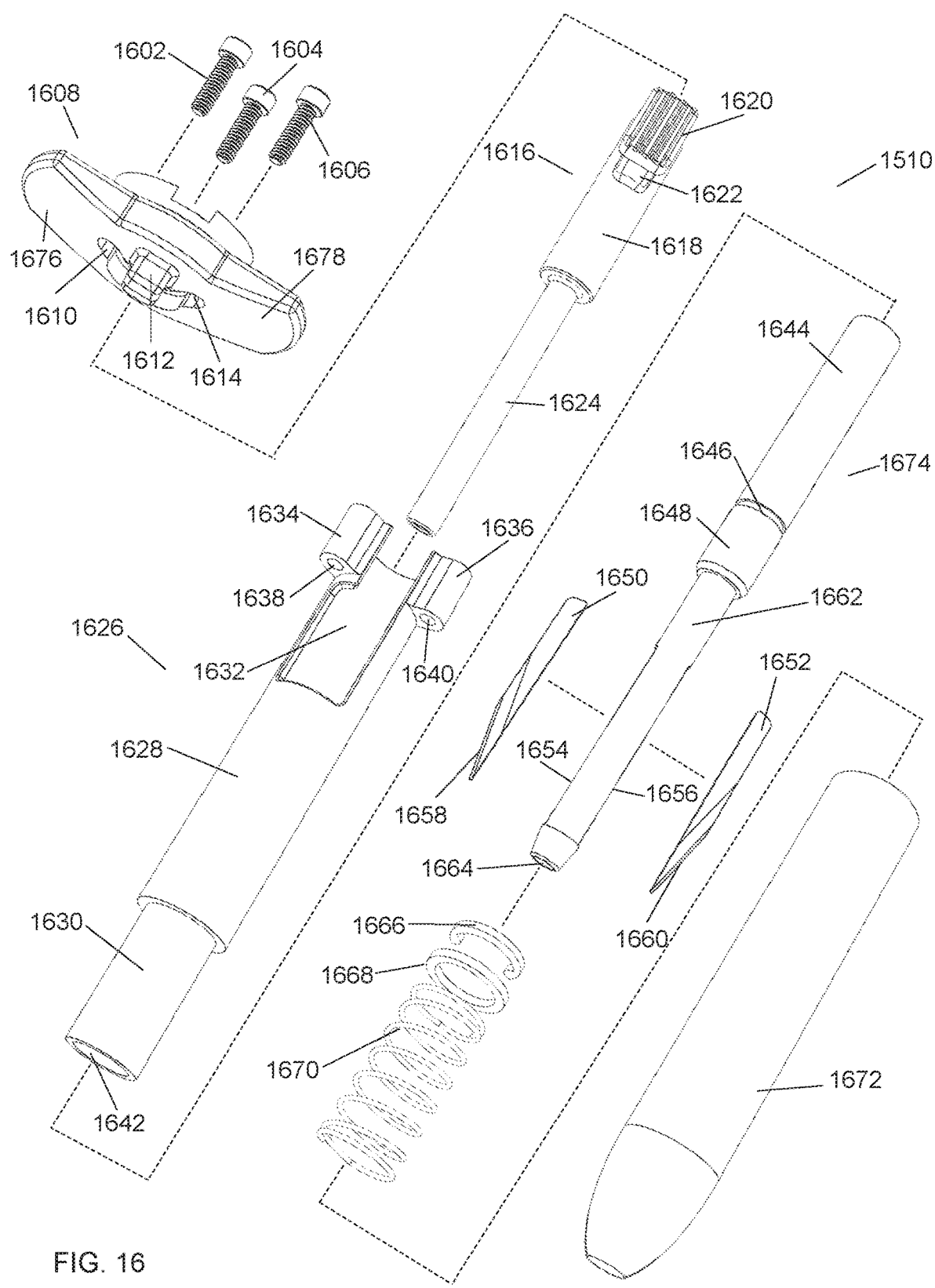
FIG. 16 illustrates an exploded view of an obturator assembly of another alternate embodiment of an insertion device according to aspects of the present invention.

FIG. 16 illustrates an exploded view of an obturator assembly of another alternate embodiment of an insertion device according to aspects of the present invention.

As shown in the figure, obturator assembly 1510 includes obturator cap 1608, pushrod 1616, obturator top 1626, blade assembly 1674, and obturator bottom 1672.

Obturator cap 1608 further includes connectors 1602-1606, holes 1610-1614, and flanges 1676 and 1678.

Pushrod 1616 further includes pushrod top 1618, tab 1620, tab stem 1622, and pushrod bottom 1624.

Obturator top 1626 further includes obturator body 1628, obturator stem 1630, slot 1632, flanges 1634, 1635 (not shown), and 1636, holes 1638, 1639 (not shown), and 1640, and opening 1642.

Blade assembly 1674 further includes blade assembly top 1644, retention slot 1646, blade assembly middle 1648, blade 1650, blade 1652, undercut 1654, undercut 1656, blade tip 1658, blade tip 1660, blade assembly bottom 1662, lumen 1664, retention ring 1666, washer 1668, and spring 1670.

Obturator cap 1608 is sized and configured to connect to obturator top 1626. Obturator cap 1608 is preferably substantially rigid to provide a user something to grip when performing a procedure. Therefore, obturator cap 1608 is preferably constructed from rigid plastic, metal, or composite material that will not substantially yield when pressed on by a user. Flanges 1676 and 1678 are sized and configured to provide a gripping and holding surface for the user during a procedure. As such, the geometry illustrated in FIG. 16 is one geometry that may accomplish this goal, however other geometries may be employed to provide the same functionality. Holes 1610, 1612, and 1614 are sized and configured to receive connectors 1602, 1604, and 1606, respectively. Connectors 1602, 1604, and 1606 may be any type of connector that is capable of attaching obturator cap 1608 to obturator top 1626. Non-limiting examples of connectors 1602, 1604, and 1606 include screws, rivets, bayonet connectors, and snap-fit connectors. The geometry and internal dimensions of holes 1610, 1612, and 1614 therefore may change based on the type of connectors 1602, 1604, and 1606 that are used. As a non-limiting example, if connectors 1602, 1604, and 1606 are screws, holes 1610, 1612, and 1614 may be threaded internally to mate with the screws. Alternatively, holes 1610, 1612, and 1614 may be sized to allow the screws to pass through without interference, allowing the screws to connect with holes 1638, 1639, and 1640.

Pushrod 1616 is configured to allow a user to operate insertion device 1500. Pushrod 1616 is preferably constructed from plastic, either molded or machined, but other materials may be used. Pushrod 1616 is preferably substantially rigid such that any force the user imparts to pushrod 161.6 will be transferred to other parts of insertion device 1500 instead of causing deformation of pushrod 1616. Pushrod 1616 is also preferably a single component, however in some embodiments pushrod 1616 may be constructed from multiple, separate components that are connected together.

Pushrod bottom 1624 is generally cylindrical in shape and is sized and configured to fit within lumen 1806 (shown in FIG. 18B), Pushrod bottom 1624 has a smaller outer diameter than that of pushrod top 1618. Pushrod top 1618 is generally cylindrical, and is sized and configured to fit within the inner diameter of obturator body 1628. Pushrod top 1618 and pushrod bottom 1624 are hollow and are sized and configured to allow stylet body 1504 and stylet tip 1508 pass through the hollow inner diameter. Tab stem 1622 extends from the outer diameter of pushrod top 1618 and supports tab 1620. Tab stem 1622 is also sized and configured to fit within slot 1632. Tab stem 1622 is long enough to provide enough clearance between tab 1620 and the rest of insertion device 1500 such that tab 1620 can be manipulated by a user.

Obturator top 1626 is preferably constructed from plastic, either molded or machined, but other materials may be used. Obturator top 1626 is also preferably a single component, however in some embodiments obturator top 1626 may be constructed from multiple, separate components that are connected together.

Obturator stem 1630 is generally cylindrical in shape and is sized and configured to fit within lumen 1710 (shown in FIG. 17C). Obturator stem 1630 has a smaller outer diameter than that of obturator body 1628. Both obturator stem 1630 and obturator body 1628 are hollow components, and are sized and configured to allow other components to fit with the inner diameters. Slot 1632 is sized and configured to allow pushrod 1616 to be manipulated by tab 1620 such that tab stem 1622 can travel within slot 1632 in both the longitudinal and circumferential directions. Flanges 1634-1636 protrude from the outer diameter of obturator body 1628 and contain holes 1628-1640, respectively. Flange 1635 is not shown on FIG. 16 because it is located on the outer diameter of obturator body 1628 opposite of slot 1632. Holes 1638-1640 are sized and configured to align with holes 1610-1614, respectively, such that obturator cap 1608 fits securely on obturator top 1626. Holes 1638-1640 therefore will securely connect with connectors 1602-1606. As a non-limiting example, if connectors 1602-1606 are screws, holes 1638-1640 will include an internal thread pattern matching that of the external thread pattern of connectors 1602-1606, and obturator cap 1608 can be securely connected to obturator top 1626.

Blade assembly 1674 is constructed from multiple components that are either rigidly or releasably connected. Blade assembly top 1644, blade assembly middle 1648, and blade assembly bottom 1662 may be a single component, however in some embodiments may be separate components connected together. In addition, blade assembly top 1644, blade assembly middle 1648, and blade assembly bottom 1662 may be constructed of the same materials, however in some embodiments may be constructed of different materials. As a non-limiting example, in some embodiments with different materials blade assembly top 1644 and blade assembly middle 1648 may be constructed from plastic, and blade assembly bottom 1662 may be constructed from metal. In this embodiment, blade assembly bottom 1662 would be connected to blade assembly middle 1648 by any conventional means to attach a plastic material to a metal material.

Blade assembly top 1644 and blade assembly middle 1648 are hollow, and the inner diameters of blade assembly top 1644 and blade assembly middle 1648 are sized and configured such that pushrod bottom 1624 can fit within blade assembly top 1644 and blade assembly middle 1648. Blade assembly bottom 1662 is also hollow, and the inner diameter of blade assembly bottom 1662 is the same size as lumen 1664, which is located at the distal end of blade assembly bottom 1662. Lumen 1664 is sized and configured to allow stylet body 1504 and stylet tip 1508 pass through lumen 1664.

Undercuts 1654 and 1656 are sections of blade assembly bottom 1662 where material is removed from the outer diameter of blade assembly bottom 1662 to provide for attachment locations for blades 1650 and 1652. Undercuts 1654 and 1656 are generally rectangular in cross-section to match the cross section of blades 1650 and 1652, and undercuts 1654 and 1656 do not extend all the way through the outer diameter of blade assembly bottom 1662, leaving lumen 1664 undisturbed. Undercuts 1654 and 1656 may include surface treatments that provide for easier attachment of blades 1650 and 1652. Non-limiting examples of surface treatments include sandblasting, oxide removal, and deep cleaning.

Blades 1650 and 1652 are used to penetrate tissue. Therefore, blades 1650 and 1652 may be constructed of any material that is suitable for penetrating tissue. Preferably, blades 1650 and 1652 are constructed of medical grade stainless steel, but other materials may be used. Blades 1650 and 1652 are cross-sectionally sized and configured to fit within undercuts 1654 and 1656, respectively, for assembly to blade assembly bottom 1662. Blade tips 1658 and 1660 are the sharpened edges of blades 1650 and 1652, respectively. Blade tips 1658 and 1660 may be of any geometry that can penetrate skin and underlying tissue. Non-limiting examples of blade geometries include straight beveled edge, curved beveled edge, straight serrated edge, and curved serrated edge. Blade tips 1658 and 1660 may also be angled to provide for a lower insertion force when penetrating skin. Preferably, the angle of blade tips 1658 and 1660 is between 10 degrees and 30 degrees as measured from the longitudinal axis of blade assembly 1674.

In some embodiments, blades 1658 and 1660 are assembled to undercuts 1654 and 1656, respectively, by mechanical welding. In other embodiments blades 1658 and 1660 are assembled to undercuts 1654 and 1656, respectively, by using epoxy or ultraviolet adhesive. In yet other embodiments, blades 1658 and 1660 are assembled to undercuts 1654 and 1656, respectively, by ultrasonic welding. Any other conventional method to assembly blades 1658 and 1660 to undercuts 1654 and 1656 may also be used.

Retention slot 1646 is a circumferential groove that separates blade assembly top 1644 from blade assembly middle 1648. Retention slot 1646 is sized and configured such that retention ring 1666 fits within retention slot 1646. Therefore, retention slot 1646 may include any cross-sectional geometry that matches the cross-sectional geometry of retention ring 1666 to create a snug fit. Retention ring 1666 is a resilient, c-shaped ring that may be constructed from any material that provides for flexibility during assembly but sufficient rigidity after assembly to prevent retention ring 1666 from separating from retention slot 1646.

Washer 1668 may be any conventional plastic, metal, or other type of washer used to provide a flat surface between two other components. The inner diameter of washer 1668 is sized and configured to be larger than the outer diameter of blade assembly middle 1648, and smaller than the outer diameter of retention ring 1666.

Spring 1670 may be any conventional spring made of plastic, metal, or other materials that will provide a consistent, resilient force. Spring 1670 is shown as a conventional helical spring in FIG. 16, however any type of resilient component may be used. The inner diameter of spring 1670 is sized and configured to be larger than the outer diameter of blade assembly middle 1648. The outer diameter of spring 1670 is sized and configured to be larger than the inner diameter of washer 1668.

Obturator bottom 1672 is preferably constructed from plastic, either molded or machined, but other materials may be used. Obturator bottom 1672 is also preferably a single component, however in some embodiments obturator bottom 1672 may be constructed from multiple, separate components that are connected together. Obturator bottom 1672 will be further described with reference to FIGS. 17A-C.

To assemble obturator assembly 1510, blade assembly 1674 must first be constructed. To assemble blade assembly 1674, retention ring 1666 is first attached to retention slot 1646 by aligning retention ring 1666 with retention slot 1646 and pushing retention ring 1666 against retention slot 1646. The open ends of retention ring 1666 will begin to separate in response to the assembly force. When the open ends of retention ring 1666 separate to where the distance between the open ends is larger than the diameter of retention slot 1646, retention ring 1666 will slide into retention slot 1646. The open ends of retention ring 1666 will return to their original configuration and hold retention ring 1666 to retention slot 1646.

Blades 1650 and 1652 are then attached to undercuts 1654 and 1656 as described above. Then washer 1668 passes over blades 1650 and 1652 and contacts retention ring 1666. Spring 1670 is then passed over blades 1650 and 1652 until spring 1670 contacts washer 1668, completing blade assembly 1674. Blade assembly 1674 is then placed into obturator bottom 1672.

Obturator top 1626 is assembled to obturator bottom 1672 by inserting obturator stem 1630 into obturator bottom 1672. Opening 1642 passes over blade assembly 1674 during assembly. Obturator stem 1630 is press fit into obturator bottom 1672 such that the fit between obturator top 1626 and obturator bottom 1672 is snug and obturator top 1626 cannot be easily removed from obturator bottom 1672. Pushrod 1616 is then dropped in to place. The outer diameter of pushrod bottom 1624 is smaller than the inner diameter of blade assembly top 1644, so pushrod bottom 1624 fits easily within blade assembly top 1644. Pushrod bottom 1624 will contact a shelf within the inner diameter of pushrod middle 1648, which stops pushrod 1616 from advancing further. This shelf will be shown and further described with reference to FIG. 18B. Obturator cap 1608 is then attached by aligning holes 1610-1614 with holes 1638-1640, and using connectors 1602-1606 to secure obturator cap 1608 to obturator top 1626. With obturator cap 1608 in place, pushrod 1616 and blade assembly 1674 are secured within obturator assembly 1510 and cannot be removed without first removing obturator cap 1608. To complete assembly of insertion device 1500, stylet tip 1508 is inserted through the inner diameters of pushrod 1616 and blade assembly 1674 such that stylet tip 1508 exits lumen 1664 and protrudes from the distal end of obturator bottom 1672, and then stylet assembly 1502 and obturator assembly 1510 are connected to dilator assembly 1512.

In alternate embodiments, stylet assembly 1502 may be replaced by any other device that fits with the system and may provide additional functionality. As a non-limiting example, a safety needle similar to safety needle 102 may be used if needle placement verification is desired prior to fully inserting insertion device 1500. However, for purposes of explanation, further discussion of insertion device 1500 will reference stylet assembly 1502.

In the embodiments described above, obturator cap 1608 cannot be easily removed after insertion device 1500 is manufactured, so sterilizing the components for re-use on another patient would be difficult. However, in alternate embodiments insertion device 1500 may be reusable. The proximal end of obturator top 1626 may include threads and obturator cap 1608 may include mating threads such that obturator cap 1608 may be easily removed after a procedure is complete. Removing obturator cap 1608 would allow a user to remove obturator top 1626, then remove pushrod 1616 and blade assembly 1674. The separate components could then be sterilized separately and re-assembled for use in additional procedures.

A threaded connection between obturator cap 1608 and obturator top 1626 is just one example connection that would provide for a reusable insertion device 1500. Other non-limiting examples of connections between obturator cap 1608 and obturator top 1626 that would provide the same function include bayonet connections and snap-fit connections.

In yet another embodiment, blade assembly 1674 and pushrod 1616 may be disposable, such that when insertion device 1500 is taken apart, the used blade assembly 1674 and pushrod 1616 may be disposed and a new blade assembly 1674 and pushrod 1616 may be added. Additional blade assemblies may be used that include different blade geometries or configurations. In some embodiments, the removable blade assembly and pushrod may be included in a cartridge that can be easily placed into an obturator bottom. Including a blade assembly and a pushrod in a cartridge would provide assurance that the individual parts of those components would remain together and a single cartridge could be easily manipulated by a user during assembly and disassembly.

In addition, if insertion device 1500 can be disassembled, additional obturator bottoms may be provided with different internal geometries to accommodate other types or geometries of blades. For example obturator bottom 1676 may be one of many different obturator bottoms available for use during a procedure. Another obturator bottom may include geometry to accommodate a blade assembly with wider blades with a shallower angle, and another obturator bottom may include geometry to accommodate a blade assembly with three blades instead of two.

Material selection for a reusable device may be different than that for a single use device. For example, a single use device may incorporate more plastics that do not need to withstand the high temperatures of an autoclave or steam sterilization within a hospital, while a reusable device may need to include more metals that can withstand such high temperatures.

FIGS. 17A-C illustrate isometric and cross-sectional views of an obturator bottom of another alternate embodiment of an insertion device according to aspects of the present invention. FIG. 17B shows a cross-section of obturator bottom 1672 along section A-A, and FIG. 17C shows a cross-section of obturator bottom 1672 along section 13-13.

As shown in the figures, obturator bottom 1672 further includes blade slots 1702 and 1704, lumen 1706, shelf 1708, and lumen 1710.

Blade slots 1702 and 1704 are cuts within the distal, inner sections of obturator bottom 1672 that are sized and configured to allow blades 1650 and 1652 to extend and retract during operation of insertion device 1500. Lumen 1710 is a cylindrical, open space within obturator bottom 1672. Shelf 1708 is located at the distal end of lumen 1710, and the inner diameter of shelf 1708 is smaller than the inner diameter of lumen 1710. Blade slots 1702 and 1704, lumen 1706, shelf 1708, and lumen 1710 will be further described with reference to FIGS. 18A-B.

Figure 18A:
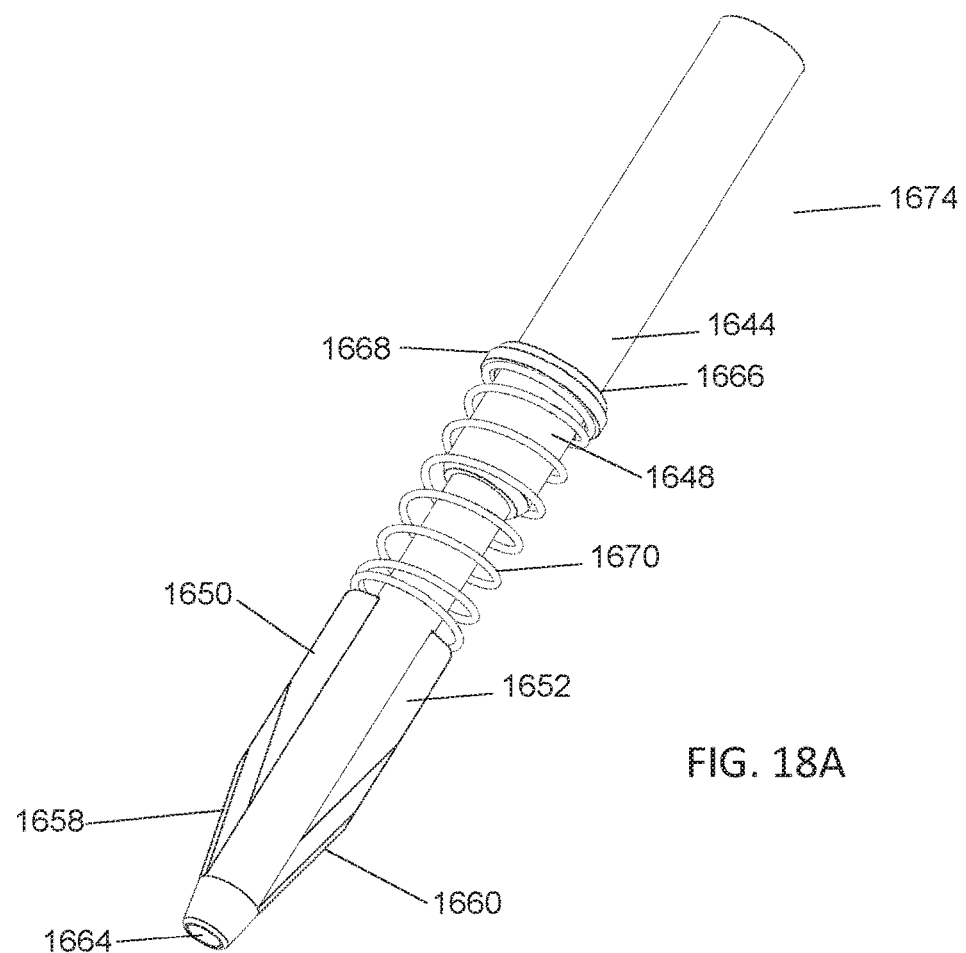
FIGS. 18A-B illustrate isometric and cross-sectional views of a blade assembly of another alternate embodiment of an insertion device according to aspects of the present invention.
Figure 18B:
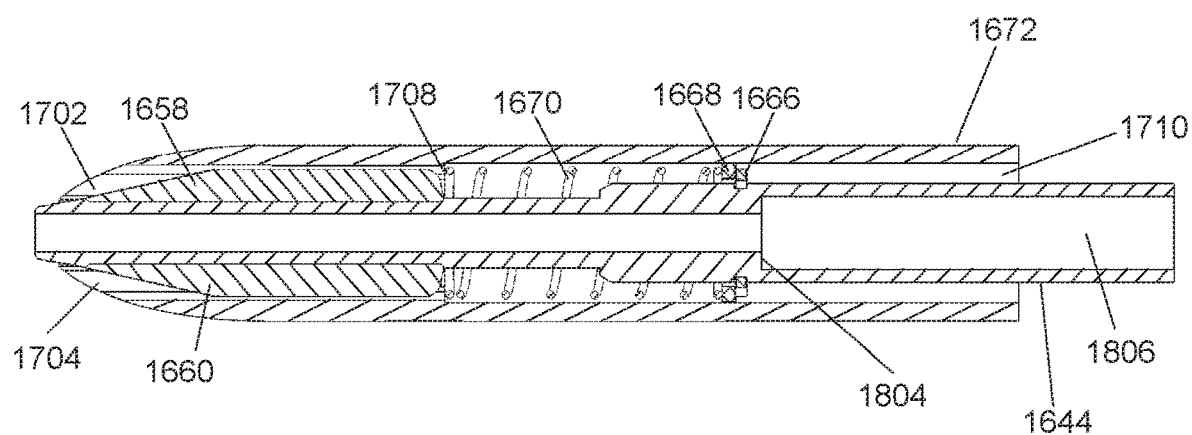

FIGS. 18A-B illustrate isometric and cross-sectional views of a blade assembly of another alternate embodiment of an insertion device according to aspects of the present invention.

As shown in the figures, the assembled blade assembly 1674 is shown in FIG. 18A. A cross-section of blade assembly 1674 assembled within obturator bottom 1672 is shown in FIG. 18B.

As shown in FIG. 18B, the inner diameter of shelf 1708 is smaller than the inner diameter of spring 1670, therefore the distal end of spring 1670 rests on shelf 1708 when blade assembly 1674 is assembled into obturator bottom 1672. The inner diameter of lumen 1710 is larger than the outer diameters of any components within blade assembly 1674, allowing blade assembly 1674 to fit easily within lumen 1710 during assembly of insertion device 1500. Blades 1658 and 1660 fit through blade slots 1702 and 1704, respectively, allowing blades 1658 and 1660 to be extended and retracted during a procedure.

Blade assembly 1674 further includes lumen 1806 and shelf 1804. Lumen 1806 is a cylindrical, open space within blade assembly top 1644. Shelf 1804 is located within lumen 1806, and the inner diameter of shelf 1804 is smaller than the inner diameter of lumen 1806.

With reference to FIG. 16, when assembling pushrod 1616 into blade assembly 1674, the outer diameter of pushrod bottom 1624 is smaller than the inner diameter of lumen 1806. However, the inner diameter of shelf 1804 is smaller than the outer diameter of pushrod bottom 1624. Therefore, when pushrod 1616 is assembled into blade assembly 1674 by inserting pushrod bottom 1624 into lumen 1806, pushrod bottom 1624 stops when it reaches shelf 1804. Pushrod bottom 1624 is not otherwise attached to blade assembly 1674 and can freely translate and rotate within lumen 1806 unless it is constrained by obturator cap 1608 and dilator slot 1516 (shown in FIG. 15).

FIGS. 19A-D illustrate various steps used to insert another alternate embodiment of an insertion device according to aspects of the present invention.

As shown in FIG. 19A, insertion device 1500 is fully assembled and ready to insert into a patient. As discussed previously with reference to other embodiments, the user will first puncture the patient's skin with stylet tip 1508 and push insertion device 1500 until blade assembly 1674 is close to the patient's skin.

Then, as shown in FIG. 19B, the user will push tab 1620 toward the distal end of insertion assembly 1500. As the user pushes tab 1620, tab stem 1622 slides within the geometry provided by dilator slot 1516. As discussed with reference to FIG. 18, when the user pushes tab 1620, pushrod bottom 1624 contacts shelf 1804, urging blade assembly 1674 toward the distal end of insertion device 1500. As blade assembly 1674 moves toward the distal end of insertion device 1500, spring 1670 is compressed and blades 1658 and 1660 extend beyond blade slots 1702 and 1704.

Next, as shown in FIG. 19C, the user maintains the downward force on tab 1620 and also urges tab 1620 circumferentially along dilator slot 1516 until tab stem 1622 contacts the side of dilator slot 1516. As discussed with reference to FIG. 18, because pushrod bottom 1624 freely rotates within lumen 1710, blade assembly 1674 does not rotate as the user rotates tab 1620.

Last, as shown in FIG. 19D, the user releases tab 1620. When the user releases tab 1620, spring 1670 imparts a force to blade assembly 1674 that urges blade assembly 1674 in the proximal direction, forcing tab stem 1622 proximally until tab stem 1622 again contacts dilator slot 1516. However, because tab 1902 of dilator slot 1516 prevents further rotation of tab stem 1622, blade assembly 1674 cannot move further to return to its undeployed configuration without additional actions by the user. At this point, blades 1658 and 1660 are exposed and the user no longer needs to manipulate tab 1620 to maintain blades 1658 and 1660 in the deployed position.

At this point, the user may continue the procedure and create the desired skin nicks by advancing insertion device 1500 until blades 1658 and 1660 enter the skin. If desired, the user may pull insertion device 1500 back, rotate insertion device 1500 90 degrees, and insert blades 1658 and 1660 into the patient again to create a larger pathway.

After the user creates the desired skin nicks, blades 1658 and 1660 can be retracted by performing the steps described with reference to FIGS. 19A-D in reverse. Once blades 1658 and 1660 are retracted, the user will then advance insertion device 1500 until reaching the desired location. After, the user can then remove stylet assembly 1502 and obturator assembly 1510 from dilator assembly 1512 at the same time, or separately as the user desires. To remove the components at the same time, the user would grip dilator assembly 1512 with one hand and obturator assembly 1510 with the other, and simply hold dilator assembly 1512 still while pulling obturator assembly 1510 until only dilator assembly 1512 is left in the patient.

As discussed with reference to FIG. 8, at this time only dilator assembly 1512 is left in the patient, and the user will typically place a catheter through the lumen of dilator assembly 1512 to reach the desired location within the body. Once the catheter is in the desired location, dilator assembly 1512 is removed from the patient, and the user completes the procedure by closing the skin around the catheter.

The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:
1. A method of accessing interior body regions, comprising:
providing an access device including a piercing device, a pushrod in slidable and rotatable communication with a blade assembly, said pushrod and said blade assembly at least partially contained within an obturator assembly, and a dilator assembly, wherein said piercing device and said obturator assembly are releasably attached to said dilator assembly;

advancing said piercing device through a skin layer and into said interior body regions;

pushing a tab of said pushrod along a slot within said dilator assembly toward a distal end of said dilator assembly, wherein said pushing compresses a spring and urges said blade assembly toward a distal end of said obturator assembly, causing at least one blade of said blade assembly to deploy through a blade slot within a distal end of said obturator assembly;

rotating said tab of said pushrod along said slot, wherein said rotating does not change the position of said at least one blade, and wherein said rotating moves said tab from a first side of said slot to a second side of said slot, said first side and said second side separated by a dilator tab;

releasing said tab of said pushrod, wherein said releasing releases said spring, said spring urging said pushrod toward a proximal end of said dilator assembly;

advancing said at least one blade by pushing said obturator assembly toward said skin layer, cutting said skin layer near an outer diameter of said piercing device to create a skin nick and increase the size of said pathway; and retracting said at least one blade by pushing said tab of said pushrod toward said distal end of said obturator assembly, rotating said tab of said pushrod from said second side of said slot to said first side of said slot, and releasing said tab of said pushrod.

2. The method of claim 1, wherein when said pushrod is urged toward a proximal end of said dilator assembly, said dilator tab prevents said pushrod from being inadvertently rotated toward said first side of said slot.

3. The method of claim 2, wherein said at least one blade remains deployed when said pushrod is on said second side of said slot.

4. The method of claim 1, further comprising advancing said piercing device, said obturator assembly, and said dilator assembly through said skin nick, wherein said advancing further comprises pushing said access device such that said obturator assembly further increases the size of said pathway deeper than said skin layer.

5. The method of claim 4, further comprising disconnecting said obturator assembly and said piercing device from said dilator assembly, leaving said dilator assembly within said pathway to provide access to said interior body regions.

6. The method of claim 1, wherein said piercing device is a safety needle assembly.

7. The method of claim 1, wherein said piercing device is a stylet needle assembly.

* * * * *